United States Patent [19]
Cabelli

[11] Patent Number: 5,814,376
[45] Date of Patent: Sep. 29, 1998

[54] GRAVURE COATING SYSTEMS AND MAGNETIC PARTICLES IN ELECTROCHEMICAL SENSORS

[75] Inventor: Michael D. Cabelli, Wilmington, Del.

[73] Assignee: Ohmicron Medical Diagnostics, Inc., Newton, Pa.

[21] Appl. No.: 488,133

[22] Filed: Jun. 7, 1995

Related U.S. Application Data

[63] Continuation-in-part of Ser. No. 372,515, Jan. 13, 1995, abandoned.

[51] Int. Cl.$^6$ ............................... B05D 1/28; B05D 3/02
[52] U.S. Cl. ........................................ 427/428; 427/372.2
[58] Field of Search .................................. 427/428, 372.2

[56] References Cited

U.S. PATENT DOCUMENTS

| | | |
|---|---|---|
| 3,900,610 | 8/1975 | McKenna . |
| 4,097,417 | 6/1978 | Pastor et al. ............................. 427/519 |
| 4,216,252 | 8/1980 | Moeller et al. . |
| 4,520,048 | 5/1985 | Ranger .................................... 427/350 |
| 4,704,296 | 11/1987 | Leanna et al. ............................. 427/9 |
| 4,738,879 | 4/1988 | Williams ................................ 427/428 |
| 5,077,912 | 1/1992 | Ogawa et al. . |
| 5,231,523 | 7/1993 | Nakaya et al. .......................... 359/56 |
| 5,547,555 | 8/1996 | Schwartz et al. ....................... 204/418 |

FOREIGN PATENT DOCUMENTS

WO9419685  9/1994  WIPO .

OTHER PUBLICATIONS

H. Benkreira et al, "Thin Films with Direct Gravure Coating", pp. 88–93, in Thin Film Coating, The Proceedings of the Second International Symposium on Coating of Thin Films, published by the Royal Society of Chemistry, Cambridge, England (1993).

"Paper–based Lightweight Panels for Automobile Interiors," Abstract from the Chemical Abstracts on–line database of the American Chemical Society; abstract of Japanese patent JP 82–69200 issued 1982, no page #s.

"Cleaning Tape for Use on Magnetic Recordings—Comprising Magnetic and Head Cleaning Layers Both on One Track," Abstract from the Derwent World Patent Index database; abstract of Japanese patent application JP 54097001 published 1979, no page #s.

"Low Viscosity Curable Organopolysiloxane Release Coating Used with Pressure Sensitive Adehesive Tape," Abstract from the Derwent World Patent Index database; abstract of PCT application WO8703537 published 1987, no page #s.

*Primary Examiner*—Shrive Beck
*Assistant Examiner*—Bret Chen
*Attorney, Agent, or Firm*—Volpe and Koenig, P.C.

[57] ABSTRACT

A method for detecting the presence of a specific analyte in a sample using an immunoassay format in which magnetic particles provide the solid phase and the signal is a dopant detectable by the change in conductivity of an electroconductive polymer coating an electrode. Additionally, magnetic devices for creating a strong force on the particles and the use of cacodylate to catalyze the production of a dopant, triiodide. Also, a gravure coating process for producing electroconductive polymer films.

6 Claims, 22 Drawing Sheets

GRAVURE COATING SYSTEMS AND MAGNETIC PARTICLES IN ELECTROCHEMICAL SENSORS

This application is a continuation-in-part of pending U.S. application Ser. No. 08/372,515 filed Jan. 13, 1995, now abandoned.

This application is divided into parts A and B, but is to be considered a single application.

FIELD OF THE INVENTION

The field of the invention are gravure processes for creating films of electroconductive polymers on solid surfaces. Additionally, the invention relates to the use of analyte-specific magnetic complexes and an electrode measurement system to detect an analyte.

PART A

FIELD OF THE INVENTION

The invention relates to the use of analyte-specific magnetic complexes and an electrode measurement system to detect an analyte.

Background

Antibodies are proteins that are produced in animals in response to molecules and molecular complexes that appear in the animal as a result of infection and tumor development. Those molecules and complexes become the cognate, i.e. target-specific, antigens for the antibodies they elicit. An immunoassay is a quantitative or qualitative method of analysis which relies on the specific reaction between an antibody and its cognate antigen. Immunoassays have been used for, among other things, environmental analysis using antibodies against herbicides, pesticides, or other environmental contaminants.

Two commonly used immunoassays formats are the sandwich assay and the competitive assay. In both formats, an analyte-reactive antibody is typically linked to a solid phase. In both formats, a reporter conjugate is required. In the sandwich assay, the reporter conjugate is an analyte-specific antibody linked to a reporter moiety capable of producing a detectable signal. As a result, in the sandwich assay, the two antibodies can sandwich an analyte molecule, one antibody linking it to the solid phase, the other antibody generating a detectable signal.

In a competitive assay, the reporter conjugate is an analyte molecule (or structural analog thereof) conjugated to a reporter moiety. Analyte present in a test sample will either compete with or displace the reporter conjugate from the antibody bound to the solid phase.

Immunoassay principles have been combined with electrosensor technology through the use of magnetic particles as the solid phase in the sandwich and competition assays. Yang et al. (Bio/Technology vol. 12, 193–194, 1993) disclosed the use of magnetic particles in a sandwich immunoassay format that relies on the localization of both a precursor molecule and a reporter moiety in the immediate vicinity of an electrode, so that the electrode drives the electron transfer between the precursor and the reporter moiety, resulting in emission of a detectable photon by the reporter moiety.

In a sandwich immunoassay format (Forrest et al., U.S. Pat. No. 4,945,045; see also, Clin. Chem. vol 31, 1449–1452, 1985), analyte was sandwiched between a magnetic particle-bound antibody and a reporter conjugate in which antibody is coupled to the enzyme, glucose oxidase. The entire magnetic complex was localized at an electrosensor electrode surface. The glucose oxidase converted ferrocene to a reduced form. The ferrocene was reoxidized at the electrosensor electrode surface as part of an electron transfer reaction, the resulting current being an indicator of the presence of analyte. The electrode used by Yang et al. was made of metal and was not coated with an electroconductive polymer. Forrest et al. recommended either a graphite or metal electrode. Neither system was disclosed to be useful in systems where the final product of the assay system was a dopant (e.g., the ion, $I_3^-$) that diffuses into an electroconductive polymer layer on an electrode assembly so as to alter the electroconductivity of the electrode assembly.

BRIEF SUMMARY OF THE INVENTION

One of the present inventions is a method for detecting the presence of a specific analyte in a sample using an assay format in which magnetic components, such as magnetic particles with antibodies on their surfaces, provide an analyte-binding solid phase and the signal is generated by a dopant that changes the conductivity of an electroconductive polymer coating on an electrode.

A related invention is the use of a magnetic device comprised of an array of magnetic pole-pieces of high relative permeability alternating with appropriately oriented magnetic structural elements to provide a focussed magnetic field that will attract the magnetic components used in an assay to the surface of a receptacle, such as an electroconductive cell.

A further related invention is the use of cacodylate to generate a triiodide dopant from hydrogen peroxide.

BRIEF DESCRIPTION OF THE DRAWINGS

FIG. 8 shows the base the platform unit of FIGS. 8–11.

DETAILED DESCRIPTION

GLOSSARY AND DISCUSSION OF TERMS USED

Figure 1:
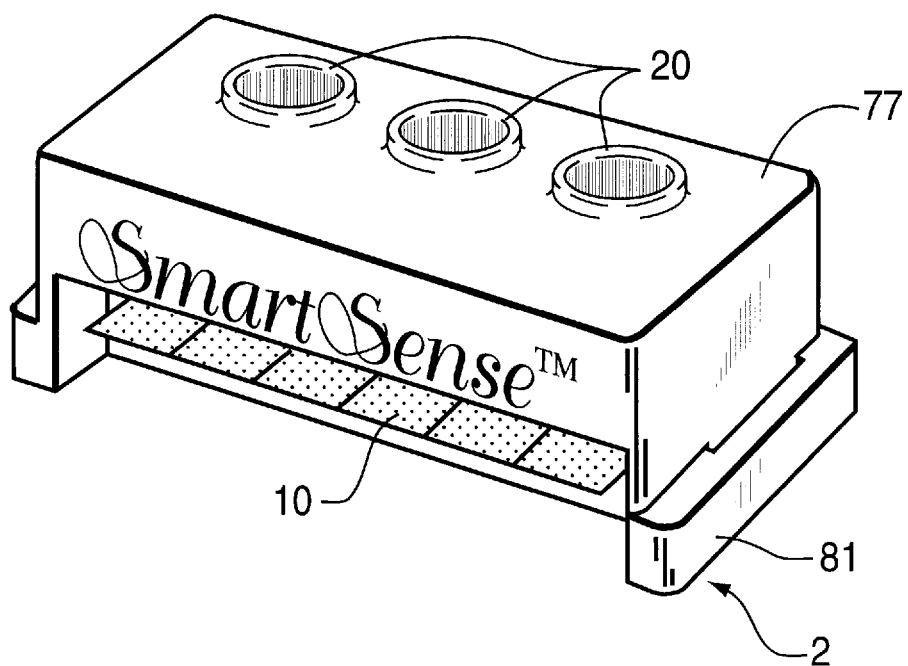
FIG. 1 is a perspective view of an electrochemical sensor.

An "electroconductive polymer" is a polymer whose conductance or capacitance can be changed by chemical oxidization or reduction, thermal excitation, optical excitation, or other physical excitation. Electroconductive polymers and their mechanism of action are disclosed and discussed by M. G. Kanatzidis et al., *Chemical & Engineering News*, Dec. 3, 1990, pp. 36–54. For sensors, oxidative doping converts an electroconductive polymer from a lower conducting to a higher conducting state. Reductive doping is also possible, however.

The spectrum of polymers that are electroconductive is very broad. They include, but are not limited to, polyacetylene, polypyrrole, polythiophene, poly(3-alkylthiophene), polyphenylene sulfide, polyphenylene vinylene, polythienylene vinylene, polyphenylene, polyisothianonaphthene, polyazulene, polyfuran, polyanaline, and derivatives of the foregoing.

Dopants are molecular species that react with an electroconductive polymer so as to change the conductivity of that polymer. Examples of dopants include, but are not limited to, $I_3^-$, $BF_4^-$, $ClO_4^-$, $FeCl_4^-$, $NOPF_6^-$—, and $N_2H_4$.

An "electroconductive sensing element" is part of a sensor whose electrical properties change in response to the presence of an analyte. The change may be due to the analyte interacting directly with the sensing element or due to the analyte triggering the production or diminution of a substance that interacts directly with the sensing element. Examples of sensing elements are those made of metal and those made of electroconductive polymers.

An "analyte" is a substance that an analytical procedure seeks to detect and quantify. Some analytes (e.g., $Na^+$) can interact directly with a sensing element and cause detectable changes in that sensing element's electrical properties. Some analytes can be detected because they trigger or inhibit chemical or biochemical reactions that generate dopants (e.g., $I_3^-$) that affect the electrical properties of sensing elements.

An "electronic instrumentation unit" is any measuring device that responds to changes in the electronic properties of the sensing element, cell electrode system, or the test solution in a cell; e.g., changes in resistance, capacitance, field strength, ionic conductivity, or solution impedance (impedimetry).

ASPECTS OF THE INVENTION

The competitive assay aspect of the invention is a method for detecting or measuring the concentration of an analyte with an electrochemical sensor, said sensor comprising a sensor cell for receiving a solution, said sensor cell comprising an electrode assembly element that has a polymer surface, said polymer surface comprising an electroconductive polymer whose conductance or capacitance is changed when it reacts with a dopant, said method comprising the steps of:

(1) creating an assay suspension comprising a first solution and a magnetic complex suspended in said first solution, said magnetic complex comprising an analyte bound to a magnetic component, said first solution comprising a reporter conjugate that is not bound to either said magnetic component or said analyte but is bindable to said magnetic component if analyte is not bound to said magnetic component, (2) separating the first solution from the magnetic complex, (3) contacting, in a sensor cell, the magnetic complex with a second solution, said second solution comprising a reaction substrate (such as glucose) and reagents (a possible set is exemplified in Examples 1 and 2) that in conjunction with said reporter conjugate can convert said reaction substrate to a dopant that changes the conductance or capacitance of the electrode assembly; and (4) measuring during step (3), after step (3), or both during and after step (3), the conductance or capacitance of the electrode assembly, wherein during step (3) the magnetic complex is kept by a magnetic force at a location at or near the polymer surface of the electrode surface.

In the competitive assay, in step (1), as to the order of addition of the analyte, the magnetic component, and the reporter conjugate, in creating the suspension, it is often preferable that the analyte be added to a solution before the reporter conjugate or the magnetic component is added, and that the reporter conjugate be added to the solution before the magnetic component is added.

A sandwich assay aspect of the invention is a method for detecting or measuring the concentration of an analyte with an electrochemical sensor, said sensor comprising a sensor cell for receiving a solution, said sensor cell comprising an electrode assembly element that has a polymer surface, said polymer surface comprising an electroconductive polymer whose conductance or capacitance is changed when it reacts with a dopant, said method comprising the steps of:

(1) creating an assay suspension comprising a first solution and a magnetic complex, said magnetic complex comprising a magnetic component, an analyte bound to said magnetic component, and a reporter conjugate bound to said analyte, (2) separating the first solution from the magnetic complex, (3) contacting, in a sensor cell, the magnetic complex with a second solution, said second solution comprising a reaction substrate and reagents that in conjunction with said reporter conjugate can convert a reaction substrate to a dopant that changes the conductance or capacitance of the electrode assembly; and (4) measuring during step (3), after step (3), or both during and after step (3), the conductance or capacitance of the electrode assembly; and wherein during step (3) the magnetic complex is kept by a magnetic force at a location at or near the polymer surface.

In both the competitive assay and sandwich aspects of the invention, the magnetic component will comprise a magnetic particle and, attached to that particle, one or more moieties that will specifically bind to the analyte. Such analyte-binding moieties include but are not limited to antibodies, nucleic acids (which hybridize to nucleic acid molecules of complementary base sequence), ionophores, lectins, and streptavidin.

In the competitive assay aspect of the invention, the reporter conjugate will comprise a reporter moiety bound to an analyte molecule or structural analog thereof In the sandwich assay aspect of the invention, the reporter conjugate will comprise a reporter moiety bound to molecule that is capable of binding to the analyte. In either case, the reporter moiety will, in the detection step of the assay, be one that is required to produce a dopant that changes the conductance or capacitance of the electrode assembly.

In both the competitive assay and sandwich assay aspects of the invention, the contacting in step (3) is preferably achieved by adding the reaction substrate after adding the set of reagents that in conjunction with the reporter conjugate convert the reaction substrate to the dopant. It is also preferred that step (2), the separation step, be done while the magnetic complex is exposed to and localized by the magnetic force. It is further preferred that after step (1) and prior to step (2), a step (1a) is added as follows:

(1a) attracting the magnetic complex to a surface in said sensor cell by exposing said magnetic complex to a magnetic force.

In one preferred embodiment, the electrode assembly element forms part or all of the sensor cell floor. In another preferred embodiment, the electrode assembly element is a probe that is inserted into the cell through the open top of the cell, and may be inserted at any time prior to step (4). The probe may be inserted so that it is adjacent to and parallel to the wall of the cell and at right angles to the floor of the cell; in such a case, a magnetic device or devices would be parallel and close to that probe and wall rather than parallel and close to the floor of the cell.

The magnetic particles that are part of the magnetic components comprise a core magnetic material (for example, iron oxide) and a surface that is modified to provide chemical groups to which antibodies can be attached through highly stable connections such as covalent bonds. In order to achieve high precision, the size of the particles must be controlled so that the particles (and therefore the magnetic components and magnetic complexes) are small enough to remain evenly dispersed during the performance of a test without additional mixing yet large enough to be effectively localized with available magnets.

In a preferred enzyme-mediated development step, the enzyme glucose oxidase first converts glucose, $H_2O$ and $O_2$ to gluconic acid and hydrogen peroxide. Then the hydrogen peroxide converts $I^-$ to $I_2$ which further complexes with $I^-$ to form the dopant $I_3^-$. The $I^-$ to $I_2$ reaction is catalyzed by an appropriate complex (e.g., cacodylate or molybdate.)

Alternatives to glucose oxidase include alcohol oxidase, L-amino acid oxidase, cholesterol oxidase, creatine hydrolase, creatinase, sarcosine oxidase, galactose oxidase, B-galactosidase, and maltase.

In a preferred format, three cells are run simultaneously in the same sensor. One cell contains the sample (with an unknown analyte concentration), and the other two cells contain solutions of known analyte concentration (one of which might have an analyte concentration equal to zero). In this format, the change in conductance, capacitance, or current, of the sample cell is compared to the change in conductance, capacitance, or current, of cells with known analyte concentrations (standard concentrations) to determine if the sample is above or below the standard concentration.

The use of antibody-coated magnetic particles in conjunction with an electrode measurement system provide several important advantages over assays that employ antibody-coated test tube surfaces:

1) The fact that the antibody-coated magnetic particles can be prepared, stored, and shipped, independently of the sensor that has the electrode allows optimal conditions for processing, storage and shipping.

2) Magnetic particles suspended in aqueous solution provide a large surface area to volume ratio for analyte-antibody binding, thereby allowing a faster reaction.

3) Suspended magnetic particles are free to diffuse, a factor that contributes to faster reaction kinetics.

4) By applying a magnetic field, the magnetic particles can be concentrated near an electrode, thereby allowing the reaction products to reach the electrode surface's electroconductive polymer more quickly and efficiently;

5) The user can control the time at which the particles, and therefore the particle-bound antibodies enter into the reaction;

6) Magnetic particles can be uniformly coated and pipetted accurately in order to ensure that the same amount of antibody is present in each cell, whereas it is difficult to precisely coat tube surfaces with antibodies;

7) The user has a choice, for a given sensor, which analyte he or she wants to test for.

Until the invention was tested, it was unclear whether the following problems would exist and make the invention impractical:

(1) Because the magnetic particles contain iron species, it was uncertain whether contaminants from the particles would affect the electrode chemistry, causing an effect on the baseline signal of the electrodes. Our tests showed, however, that under the conditions tested, such as those in Example 1, addition of particles did not effect the baseline signal of the electrodes.

(2) It was not clear that reporter moieties, such as enzymes, located on particles of 1 $\mu$ diameter (the approximate diameter of the magnetic particles used in the Examples) and thereby not directly located on the surface of the electrode would even generate a detectable signal.

(3) It was uncertain whether the magnetic particles would "block" the electrodes. Electrode "blocking" would cause a variable change in system impedance. However, under the conditions of our tests, such as those in Example 1, no such effects of the particles on the system impedance was observed.

(4) It was uncertain whether the proximity of a magnetic field near the electrodes would affect the noise levels or linearity of the system. However, under the conditions of our tests, such as those of Example 1, no such effect was observed.

A related invention is a method for detecting an analyte in an apparatus that comprises an array (e.g., a linear array) of receptacles of similar structure, each of said receptacles comprising an inner surface, said method comprising the steps of:

(1) creating, in a receptacle of said array, a suspension of a magnetic complex in a solution, said magnetic complex comprising an analyte and a magnetic component bound to said analyte, (2) attracting said magnetic complex to said surface by exposing it to a magnetic force, and (3) detecting said magnetic complex, wherein the magnetic force is created by a magnetic field device that comprises an array of magnetic pole-pieces, each consecutive pair of pole-pieces in the array separated from each other by a magnetic structural element, (each of said pole-pieces preferably having a relative magnetic permeability greater than $10^5$) the separation between successive pole-pieces in the array of pole-pieces being the same as the separation between successive receptacles in the array of receptacles.

A further related invention is a separation apparatus for detecting an analyte in a receptacle, said apparatus comprising an array of receptacles of similar structure, each of said receptacles comprising an inner surface, said apparatus further comprising a magnetic field device that comprises an array of magnetic pole-pieces, each consecutive pair of pole-pieces in the array separated from each other by a magnetic structural element (either ferromagnetic or electromagnetic), each of said pole-pieces preferably having a relative magnetic permeability above $10^5$) the separation between successive pole-pieces in the array of pole-pieces being the same as the separation between successive receptacles in the array of receptacles.

The magnetic structural elements in the structural element array are oriented so that a pole-piece will either be adjacent to the two South poles of two magnetic structural elements or adjacent to the two North poles of two magnetic structural elements.

The magnetic pole-pieces are used to focus and control the magnetic field created by the magnetic structural elements. The orientation of the magnetic structural elements results in a concentration of the magnetic field at locations near the outer surfaces of the pole-pieces. Because those locations are also the locations of the magnetic particles in the cells of the electochemical sensor, the magnetic field device will exert the required magnetic force on those particles. The pole pieces may be made of any solid material but are preferably made of one that has a relative magnetic permeability above $10^5$.

Figure 26:
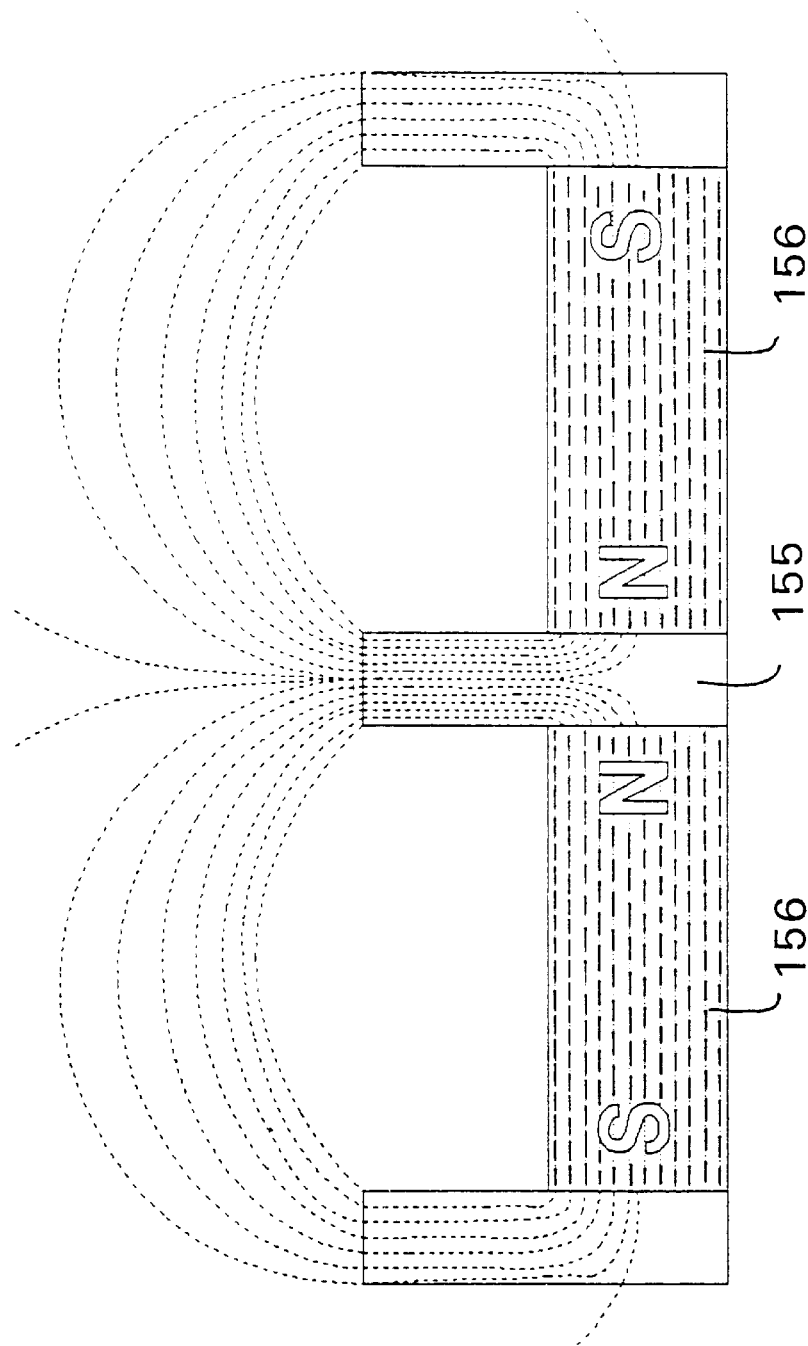
FIG. 26 schematically illustrates how magnets and a pole piece combine to create a magnetic field.

FIG. 26 schematically illustrates how inserting a pole-piece (155) between, and therefore adjacent to, the North poles (designated by the letter "N") of two magnetic structural elements (156) creates a relatively large concentration of field lines (the dashed lines) at locations above the pole piece, i.e., the locations where there would be magnetic particles in the cells of the sensor.

The magnetic field device may be used in conjunction with a magnetic focussing device. The magnetic focussing device may, for example, be attached to the underside of the electrochemical sensor or fit within the lower portion of the sensor. The sensor along with the focussing device may then be slid back and forth along a surface, one position on the surface sufficiently removed from the magnetic field device so as to permit assay reactions to proceed with uniformly distributed magnetic particles, another position on the surface bringing it in proximity to both a docking unit for electrical measurements and a magnetic field device.

A magnetic focussing device was used in Example 2, but not Example 1, below. In Example 1, the position of the magnetic field device relative to the sensor was similar to the position of the focussing device relative to the sensor in Example 2.

It is preferred that the pole-pieces of the magnetic field device have a relative magnetic permeability greater than $10^6$. Preferred materials for such pole-pieces are ferromagnetic ones such as silicon-iron, iron, steel, cobalt, nickel, magnetite, and some alloys of manganese. In the magnetic field device used in Examples 1 and 2, the material was silicon core iron.

The relative magnetic permeability of a material (or medium) is the absolute permeability of the material (or medium) divided by the absolute permeability of vacuum.

Preferred material for magnetic structural elements are: neodymium-iron-boron (used in Examples 1 and 2), samarium cobalt, and other rare earth magnets.

The purpose of the focussing device is to bridge the spatial gap between the magnetic field device and the sensor cells of the electrochemical sensor by extending the focussed magnetic field. As a result, the pole pieces of the focussing device should have a high relative magnetic permeability (preferably greater than $10^5$). Furthermore, a magnetic focussing device, because it will be in the proximity of a sensor cell under conditions where it is not desired that any magnetic force be exerted on the contents of that cell, should optimally not generate a magnetic field when not in close proximity to the magnetic field device. That goal is achieved by constructing a focussing device in which the pole-pieces have a low residual flux density and using nonmagnetic separator elements to separate those pole-pieces. Preferred pole-pieces are silicon-iron alloys, and Mu-metals. However, soft iron was used in Example 2 even though it is not preferred for repeated use. Aluminum was used in the Example 2 as the material for the nonmagnetic separators. Preferred separator materials also include plastics.

The pole-pieces of the focussing device will be in an array spaced in the same manner as the pole-pieces of the magnetic field device; as a result, the pole-pieces of the two devices may be aligned along side each other.

Usually it is preferred that the ends of the magnetic field device are pole-pieces (as in the Figs. here). However, slightly higher field gradients can be obtained by adding a magnetic structural element at each end of the device.

A further related invention is a method for detecting an analyte with an electrochemical sensor, said sensor comprising a sensor cell (but preferably three or more of identical shape and size) for receiving a solution, said sensor cell comprising an electrode assembly element that has a polymer surface, said polymer surface comprising an electroconductive polymer whose conductivity is changed when it reacts with triiodide, said method comprising the steps of:

(1) creating a solution (preferably aqueous) that comprises cacodylate, (2) incubating the analyte with reagents that, in the presence of the analyte, will create hydrogen peroxide, (3) incubating the hydrogen peroxide in the presence of part or all of the solution created in step (1) so as to produce triiodide in the sensor cell, (4) allowing the triiodide to react with the electroconductive polymer; and (5) detecting the change (or time rate of change) in the capacitance or conductance of the electrode assembly during the production of the triiodide.

The solution created in step (1) should be an aqueous solution. A preferred solution is cacodylate in water. If the solution created in step (1) does not have catalytic activity that, in the presence of $H_2O_2$, will result in the conversion of $I^-$ to $I_2$, then the time period between step (1) and step (2) is preferably between one and two days. Whether or not the solution created in step (1) will require the one-to-two day incubation will depend on the batch of cacodylate purchased.

The Examples below were performed with atrazine as the analyte; other analytes can be tested for.

Particularly suited analytes include pesticides and herbicides, especially those that are inorganic or organic molecules (contains carbon and hydrogen; they may also contain other elements, such as but not limited to oxygen, nitrogen, halogens, sulfur and phosphorus) with a molecular weight of about 2000 daltons or less. Antibodies against such analytes or their analogs can be produced by linking them to a carrier such as bovine serum albumin and injecting animals so as to create polyclonal antibodies or monoclonal antibodies.

Environmental contaminants that are the products or byproducts of chemical synthesis are also of particular interest; examples include polychlorinated biphenyls (PCBs), polynucleararomatic hydrocarbons (PAHs), dinitrotoluene, as well as benzene, toluene, ethylbenzene, xylene, (BTEX) and their derivatives.

Other environmental contaminants of interest are metal ions.

Another general class of important analytes are those of medical diagnostic interest. A wide variety of antibodies that are specific for analytes of medical interest are commercially available. Among the most important are antibodies that are specific for particular viruses or other microorganisms, or the toxins synthesized by microorganisms. Alternatively, blood cell-typing may be done. Frequently, the antibody's target is a protein or glycoprotein. Indeed, it can be of interest to test a person's bodily fluid (e.g., blood, serum, urine) for the presence of a herbicide, pesticide, metal ion, or the product or byproduct of chemical synthesis.

The invention can, however, be applied to the detection of almost any molecule or molecular compound, because it is possible to raise antibodies against the vast majority of substances and it is possible to link glucose oxidase (or other enzymatic reporter moiety) to virtually all of those antibodies. In the case of most substances, it is expected that a conjugate between that substance and glucose oxidase (or other reporter enzyme) should be possible.

Antibodies against all, or almost all molecules and molecular complexes may be obtained, as evidenced by the enormous range of monoclonal and polyclonal antibodies now available. (See, for example: Linscott's directory published by Dr. William Linscott, 4877 Grange RD, Santa Rosa, Calif. 95404; the American Type Tissue Collection catalogue, Rockville, Maryland; catalogue of Calbiochem, La Jolla, Calif.; the catalogue of Sigma Immunochemicals, St. Louis, Mo.)

The magnetic particles bound to antibodies specific for the following compounds (as well as horseradish peroxidase conjugates that react with those antibodies) are obtainable from Ohmicron, Inc., Newtown, Pa. as part of their RaPID-Dassay® kits: Alachlor, Aldicarb, Cyanazine, 2,4-D (including the propylene glycol, ethyl, isopropyl, methyl, butyl, and sec-butyl esters), Atrazine, Benomyl, Carbendazim, Captan, Carbofuran, Metolachlor, Procymidone, Carbaryl, Chlorothalonil, Chlorpyrifos, cyanazine, paraquat, pentachlorophenol, and polychlorinated biphenyls.

Other companies that sell immunoassay kits with antibodies against environmental contaminants include BioDesign, (Kennebunkport, Me.), Guilday (Surrey, England), and Millipore (Bedford, Mass.).

Antibodies specific for a compound can also be used to detect structural analogues of that compound providing the immunoreactivity for the antibodies is retained despite the structural variation. Antibodies against metals have been disclosed: e.g., Wylie et al, Proc. Natl. Acad. Sci., vol. 89, p 4104 (1992) for mercuric ions; Clarke, J. Immunological Methods vol 137 p65–72 (1991) for beryllium; Reardan et al, Nature, vol 316, p265 (1985) for some metal chelates; U.S. Pat. No. 4,772,892 for some metal chelates; Australian patent application 66357/86 for some inorganic metal salts; and PCT application WO 90/10709 for some metallic cations.

Generally, most antibodies can be bound to magnetic particles using the technology set forth in U.S. Pat. No. 4,554,088 (Whitehead et al.); see also Rubio et al *Food Agric. Immunol.* vol 3, 113 (1991)).

For purposes of a competitive assay, conjugates of an analyte (or an analogue that is a molecule structurally similar to the analyte) with glucose oxidase can be done by the same methods that were used to conjugate that analyte to a protein for purposes of creating an immunogen that generated antibodies against that analyte. For example, conjugates can be made by direct chemical reaction between the analyte atrazine (or an analogue) in which the atrazine's chlorine is replaced with a sulfur atom and glucose oxidase, via a bifunctional linker molecule, or is linked to the analyte. Alternatively, an analyte (or an analogue) and the glucose oxidase can be bound to separate molecules (such as biotin and streptavidin) which are capable of binding to each other, thereby linking the atrazine and the glucose oxidase.

For conjugating an enzyme to an antibody or conjugating an analyte (such as a hapten) to a protein, see P.Tijssen, Practice and Theory of Enzyme Immunoassays, Elsevier, Amsterdam, New York, Oxford, 1985 as well as the references cited therein.

An example of conjugate technology is disclosed in T. S. Lawruk et al, *J. Agric. and Food Chem.*, vol 41, 1426 (1993) for conjugating the a-haloacetamide, Metolachlor, to proteins and for conjugating horse radish peroxidase to the analyte.

An example of conjugate technology for haloacetamides is U.S. Pat. No. 5,147,786 (Feng et al.).

For purposes of a sandwich assay, the glucose oxidase or other enzyme can be linked to the antibody of interest by known methods that link enzymes to antibodies.

Of course, it is not always necessary to use an antibody as the analyte-specific reagent. Examples of other types of analyte-specific reagents are chelating agents for metals, ionophores, lectins for carbohydrates, streptavidin for biotin, and nucleic acid molecules (for detecting nucleic acid molecules of complementary base sequence).

Many reports disclose the detection of nucleic acids in sandwich assays (see, e.g., U.S. Pat. No. 4,486,539 of T. M. Ranki), including ones using magnetic particles.

The invention may be used with either heterogeneous (some of the materials and/or reagents used in the assay are removed prior to measuring the assay response, e.g., the conductance) or homogeneous (all materials and/or reagents used in the assay are still in the cell at the time the assay response, e.g., the conductance, is measured) formats. Analyte, conjugate, and antibody concentrations, order of addition and incubation times are optimized for different analytes. Similarly, the electrode geometry and cell volume may be changed to optimize a particular system.

ELECTROSENSOR AND MAGNETIC DEVICES

The electrosensor used in the Examples is illustrated in FIGS. 1–7, 24 and 25. Essential features of the magnetic focussing device, magnetic field device, and platform with docking unit, used in Example 2 are illustrated in FIGS. 8–23, although it will be clear to person of ordinary skill in the art that some of the illustrated features are not essential and that all features can be substituted with equivalent features.

The electrosensor used in Examples 1 and 2 had three cylindrical cells, the floors of the cells provided by the polymer-coated surface of a thin rectangular electrode assembly. The electrode assembly, under its topmost layer (an electroconductive polymer-coated surface), had an intermediate layer of strips of platinum separated by 0.05 cm separation strips made of electroconductive polymer). The base, or lowest layer, of the assembly was made of a nonconducting polymer film (polyester) upon which the platinum strips had been deposited by a sputtering process and patterned so as to create a striped base. After creating the platinum strips, the metal-striped base was coated with poly(3-n-hexylthiophene) solution so as to create a poly(3-n-hexylthiophene)-coated electrode.

The cylindrical cells were positioned with respect to the polymer-coated surface of the assembly so that each cell straddled parts of two platinum strips. The electrodes of an electronic instrumentation unit were connected separately to each strip of a straddle pair.

Figure 2:
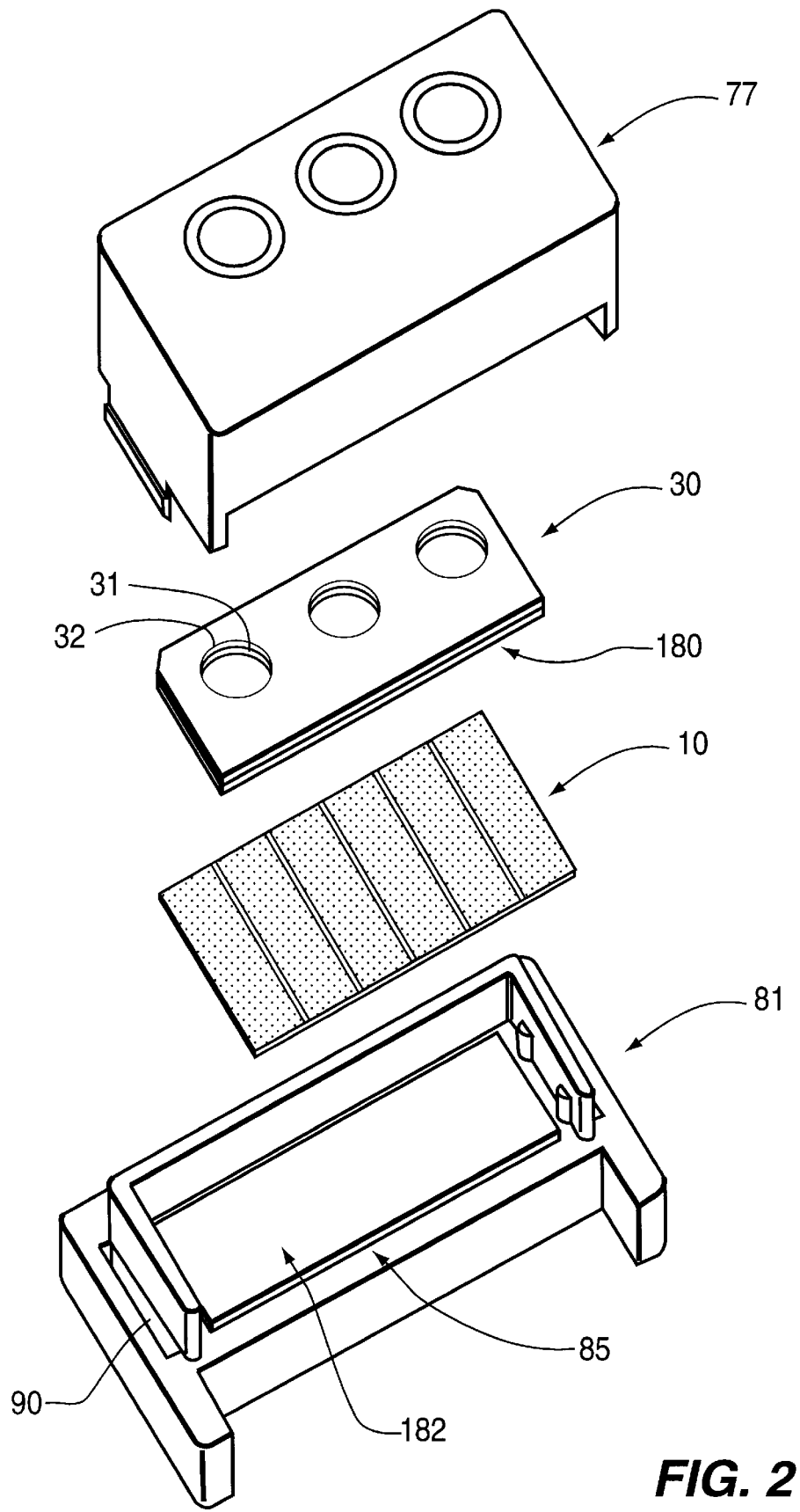
FIG. 2 is an exploded perspective view of the sensor of FIG. 1.

FIG. 1 is a perspective view of the assembled sensor (2). FIG. 2 is an exploded cross-sectional view of the sensor. FIGS. 1 and 2 illustrate that the sensor is made of four parts: a cover unit (77), a three-hole gasket (30), a base unit (81), and a flat electrode assembly (10). In FIG. 1 the rims (20) of the three sensor cells are denoted. In FIG. 2, the platform (85) of the base unit, upon which the electrode assembly lies in the fully formed sensor, and a side slot (90) in the base unit, are shown. The gasket (30) has three holes, each defined by a circular wall (32), the edge of each wall defined by a circular rim (31). The gasket was 0.076 cm. thick and the electrode assembly was 0.0127 cm. thick, almost all of it due to the nonconductive film that is the bottom layer of the electrode. In some of the drawings, the thickness of the gasket and the electrode assembly may be drawn disproportionately large (for comparison, consider that the cell diameter is about 0.80 cm.) so as to assist the reader in visualizing the sensor's construction. Similarly, the thickness of the electroconductive polymer layer and the thickness of the metal electrodes may be drawn disproportionately large compared to the thickness of the nonconductive film that forms the bottom layer.

On the underside of, and adherent to the gasket (30) in FIG. 2 there is a piece of double-sided tape (180) coextensive with the underside of the gasket and has three holes the same size as those in the gasket. The tape adheres to the top of the electrode assembly (30) in the assembled sensor. On the underside and adherent to the electrode assembly (10) there is a piece of double-sided tape (182) coexrensive with the underside of the electrode assembly. In the assembled sensor, the tape (182) also adheres to the platform (185) of the base unit (81). The pieces of two-sided tape were acrylic tape. In order to simplify them graphically, the tape is not depicted in other Figures, even though it was present in the sensor.

The cover unit and the base unit were secured to each other so as to maintain the integrity of the sensors, including the electrode assembly. The cover unit was secured to the base unit by a securing means that had two components: a protruding securing component and a receiving securing component that was an opening through which the protruding component fit. The protruding component was a latch component which can be further secured by melting or gluing.

Figure 3:
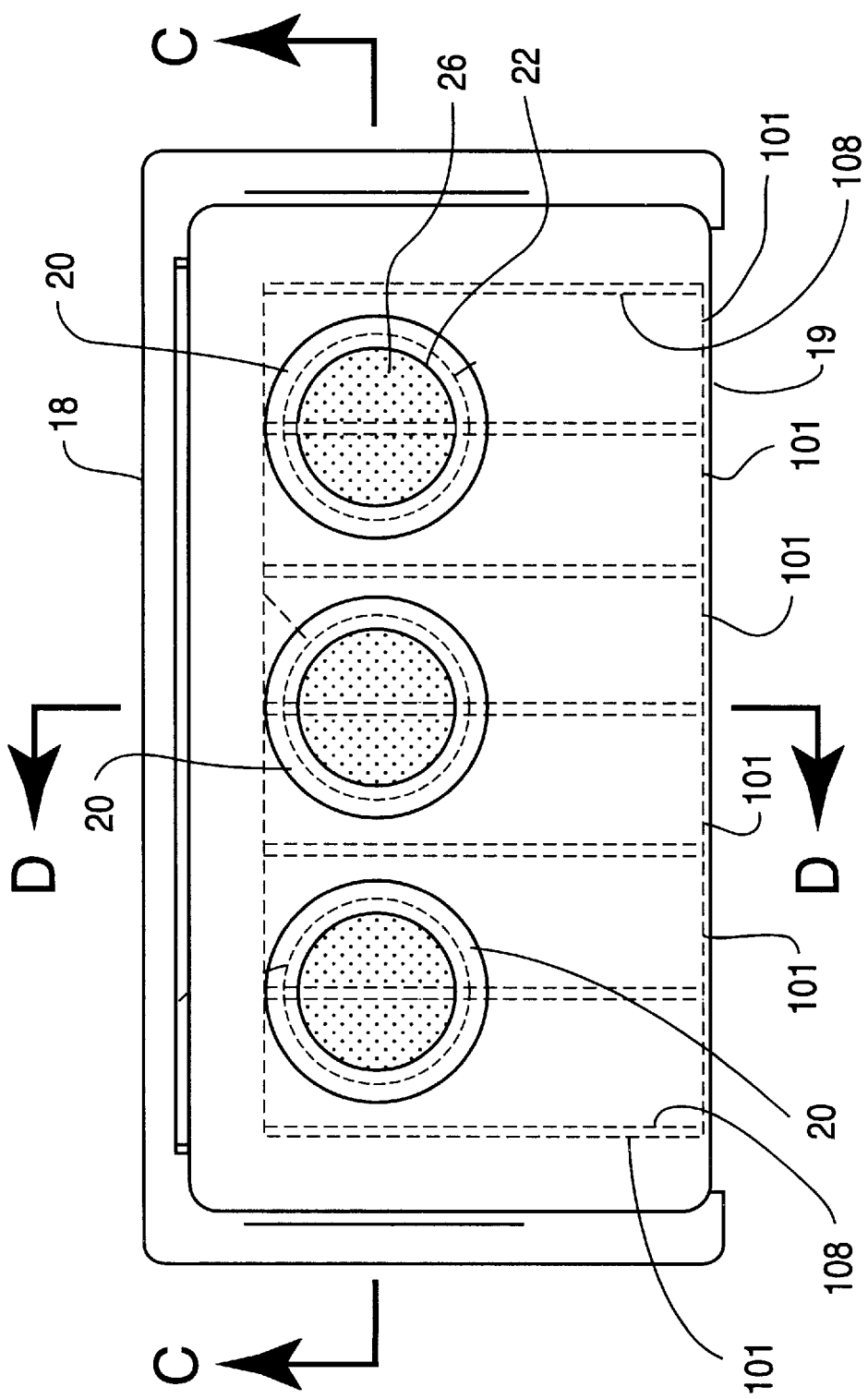
FIG. 3 is a top plan view of the sensor of FIG. 1.

FIG. 3 is a top plan view of the assembled electrochemical sensor showing the top rims (20) of three hollow cylinders, as well as the positions of the inner wall surface (22) of each of those cylinders. (The cylinders are of identical construction and, although the rims are each marked with the number 20, in some Figures a structural element common to all the cylinders may actually be marked on only one cylinder, in order to make a drawing less crowded.) The back edge of the assembled unit (18) and the front edge (19) are also indicated. In FIG. 3, selected internal features of the sensor, including the electrode assembly perimeter (101) and the outer front-to-back edges (108) of the electrode strips, are shown as dotted lines.

Each cylinder wall (22) is part of a sensor cell that acts as a receptacle within which assay steps can be carried out. The floor of each cell is provided by a portion of the electrode assembly element.

A portion of the electrode assembly that was the floor of a sensor cell is referred to as an electrode assembly element. Evident in FIG. 3 is the electrode assembly element (26) that was the floor of each cell. Each element (26; shown for one of the three identical elements) defined a circular area on the electrode assembly top surface, circumscribed by a circular rim (31) of the gasket (30) shown in FIG. 2. The electrode assembly elements, and therefore the receptacles for which they supply a floor, are in a linear array; e.g., they fall on a line that passes through their centers.

Two of the sensor's parts (cover unit and base unit) were made of plastic by injection molding and have been designed for ease of mold manufacture and optimization of electrode surface area.

Each sensor cell was a 1.52 cm deep hollow cylinder seated on the electrode assembly and centered on one of the three electrode pairs. The separation between the axes of symmetry of two adjacent cylindrical cells was 1.461 cm.

Figure 4:
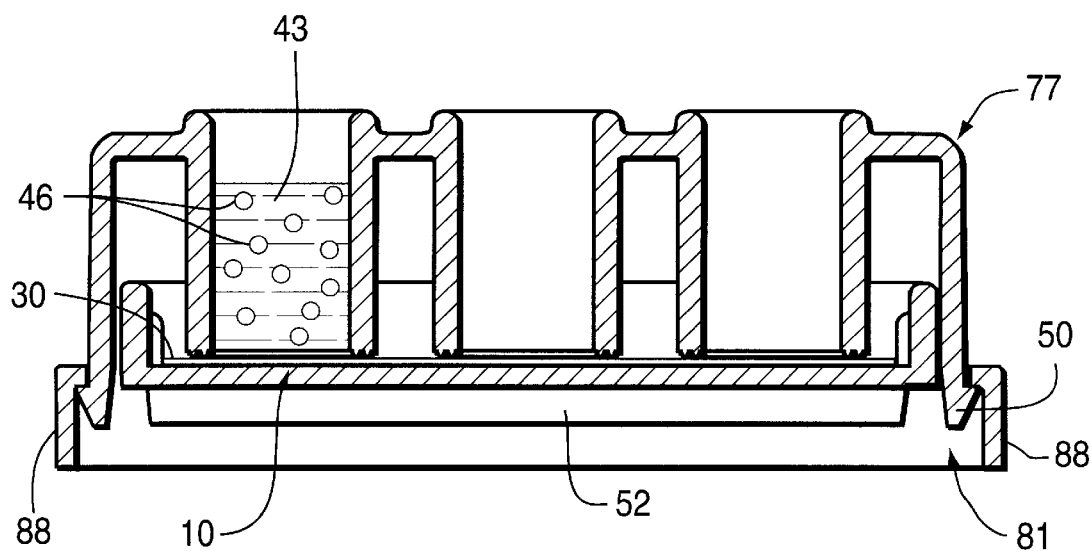
FIG. 4 is a cross-sectional view taken along axis C—C in FIG. 3, with a suspension of magnetic complexes visible in one of the three cells.
Figure 5:
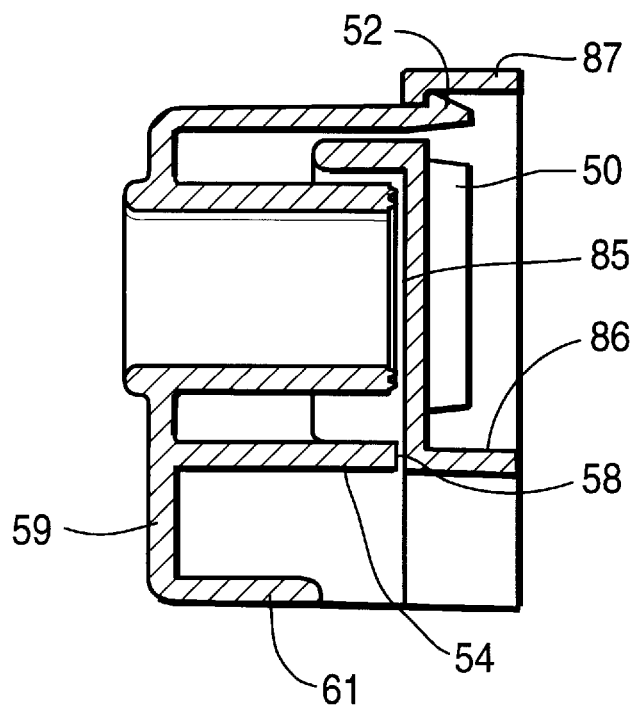
FIG. 5 is a cross-sectional view taken along axis D—D in FIG. 3, except that the electrode assembly and the pressure pad are not shown.

FIGS. 4 and 5 show two cross-sectional views of the assembled sensor, illustrating the relationships of the cover unit (77), base unit (81), electrode assembly (10) and gasket (30).

FIG. 4 is a cross-sectional view of the assembled sensor (taken along line C—C in FIG. 3). The fine structure of the electrode assembly (10), visible in the front elevational view of the electrode assembly has been omitted here. Also shown are a back protruding latch component (52) and, in cross-section, a side protruding latch component (50). The latch components fit through correspondingly positioned slots in the base unit. Also marked in FIG. 4 are the two side support walls (88), shown in cross-section, on the underside of the base unit. Eight magnetic complexes (46) shown for two of the eight complexes) suspended in solution (43) in one of the three cells are shown. The actual diameter of each particle was approximately one micron; the number in the solution numbered in the millions. As result, the complexes were disproportionately enlarged in FIG. 4 for illustrative purposes.

FIG. 5 is a cross-sectional view of the assembled sensor (taken along line D—D in FIG. 1) except that the electrode assembly (10, in FIG. 2) and the gasket (30 in FIG. 2) have been omitted even though they were present in the actual sensor. This view shows a divider wall (54). The lower edge (58) of the divider wall made essentially continuous contact with the top surface of the electrode assembly, thereby helping to keep that assembly flat. The cover segment (59) and the "hanging section" (61) are contiguous with each other and together comprised the overhang. Also shown are a side protruding latch component (50) and, in cross-section, a back protruding latch component (52). Also marked in FIG. 5 are the back support wall (87) and the front support wall (86), both shown in cross section. A magnetic focussing device will fit into a cavity created by the four support walls on the underside of the base unit.

Figure 6:
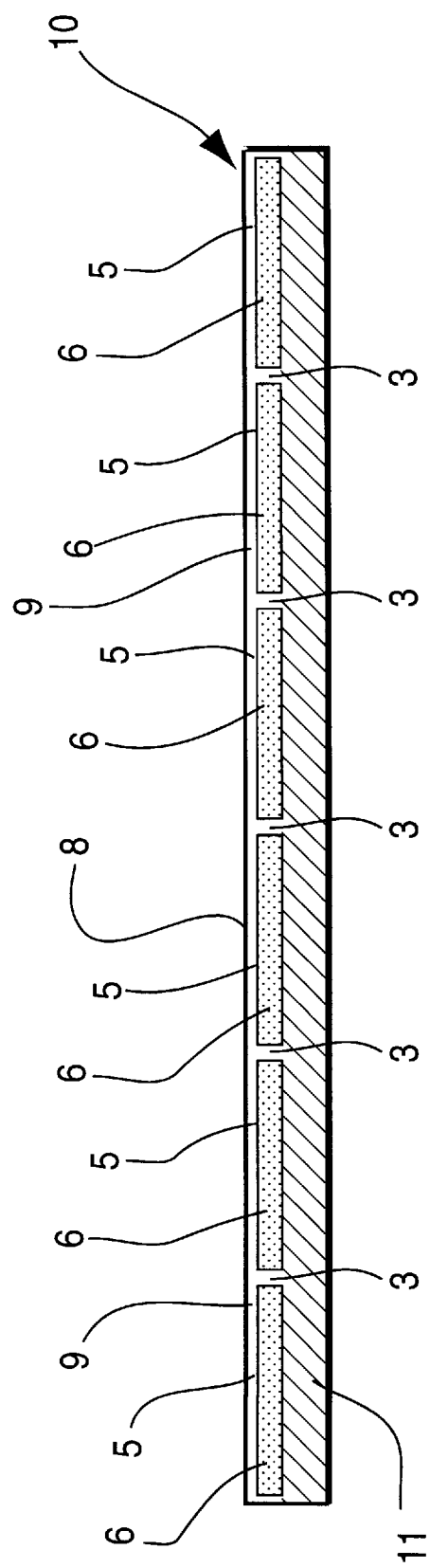
FIG. 6 is a front elevational view of the electrode assembly.

FIG. 6 shows a front elevational view of the electrode assembly (10). The upper surface (8) of the assembly was made of poly(3-n-hexylthiophene). Under this film lay six metal strips (denoted by the number, 6) each of which has an upper surface (5). The metal strips lay on a nonconductive support sheet (11), and the entire surface was coated with electroconductive polymer. The microscopically thin layer (9) of electroconductive polymer, enlarged for purposes of illustration, is denoted.

Figure 7:
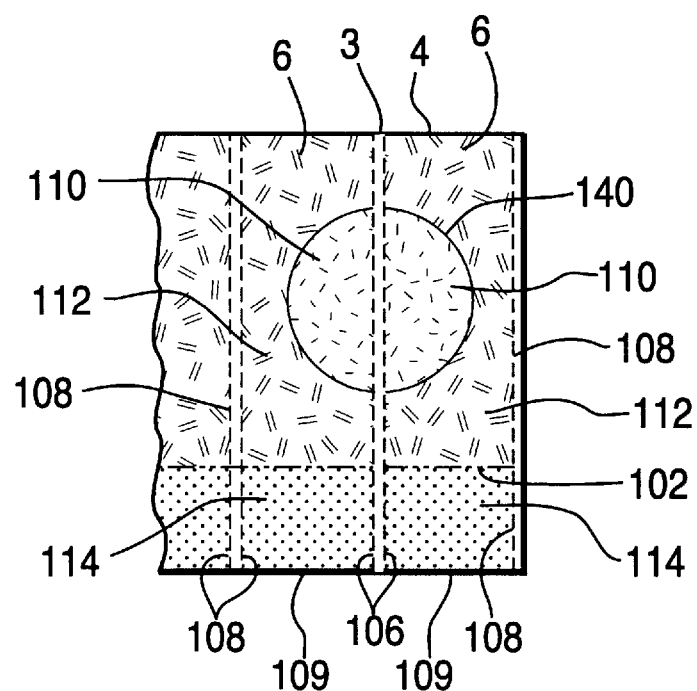
FIG. 7 is a top plan view of a portion of the electrode assembly; some of the dashed lines are added to identify schematically various functional areas of the electrodes.

FIG. 7 is a top plan view of a portion of the electrode assembly; some of the dashed lines are added to identify schematically various functional areas of the electrodes.

FIG. 7 shows in schematic fashion how each platinum electrode strip (6) of the electrode assembly (4) was divided into functional segments: a cell electrode (110), an electrical connector (112), and an access electrode (114). The cell electrode was a segment whose outer perimeter was defined by the inner front-to-back edge (106) of an electrode strip (6) and by a contact line (140) between the inner rim of a gasket and the upper electrode assembly surface (8) of that electrode. The access electrode (114) in the Figure was a segment whose perimeter was defined by the front end (109) of an electrode strip (6), by the contact line (102) between the divider wall lower edge (58) and the electrode assembly upper surface (8), by the inner front-to-back edge (106) of the electrode strips, and by the outer front-to-back edge (108) of the electrode strips.

The gasket (e.g., 0.076 cm. thick), (30; in FIG. 2), was made of a polyethylene foam (Volara, grade 060A 0031WH). Its purpose was to create a better seal between the electrode assembly surface and the rims on the lower edge of the cylinder in order to prevent leakage. Its lower layer, not shown here, is identical to the top layer.

The electrode assembly measured 2.21 cm×4.38 cm. The assembly had a set of six metal strips (2.21 cm.×0.679 cm.), and all strips were separated by a fixed spacing (0.0508 cm.) Two narrow strips (2.21 cm.×0.0254 cm.) separated the two outside metal strips from the edges of the electrode assembly.

FIGS. 8–23 illustrate a preferred embodiment of the magnetic field device and a preferred embodiment a magnetic focussing device.

Figure 8:
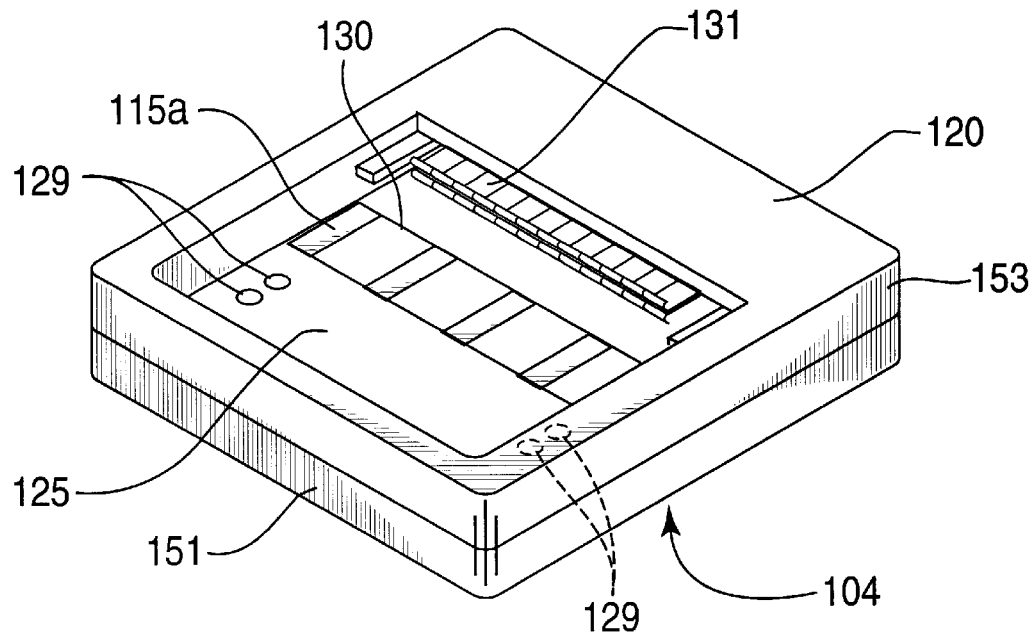
FIG. 8 is a perspective view of a platform unit.

FIG. 8 shows a platform unit (104) that contains a magnetic field device (130) and an electronic docking unit; one surface (115a) of a pole-piece of the magnetic field device is denoted numerically. Also visible are the circular surfaces (129) of four cylindrical magnets that extend into the platform and whose function is to hold a magnetic focussing device in place at an area (125) of the surface intended to receive the device when it is in the platform but not over the field device.

The platform unit can consists of a base unit (151) and cover unit (153). A portion (120) of the cover unit covers the electronic docking unit. The electrical connecting device (131) that is part of the docking unit is shown. (Internal details of the electronic docking unit, such as a printed circuit board, and holes made in the base unit in order to accommodate those parts, are not shown in the Figures.) The exposed portion of the electrode assembly (10, see FIGS. 1 and 2) can fit into the electrical connecting device thereby allowing electronic connection of the sensor to the docking unit.

In a preferred embodiment, three small LED's positioned on the top of the docking unit in parallel the sensor cells can be used to alert the user as to which sensor cell should receive materials so that the cells receive the materials in a desired sequence.

A device with multiple platform units in any desired arrangement can be made. One example is to have four units arranged end-to-end in the same device.

Figure 9:
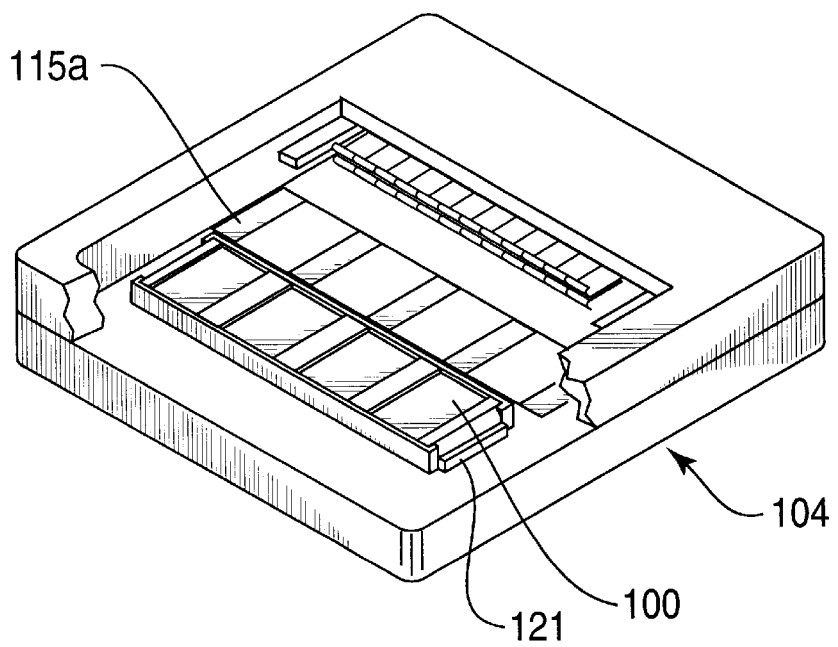
FIG. 9 is FIG. 8 modified in that part of the unit is cut away and in that a magnetic focussing device is on surface of the platform unit.

In FIG. 9, a magnetic focussing device (100) is on the platform unit's receiving surface (125) shown in FIG. 8 (but hidden from view in FIG. 9). An end rim (121) of the magnetic focussing device is visible.

Figure 10:
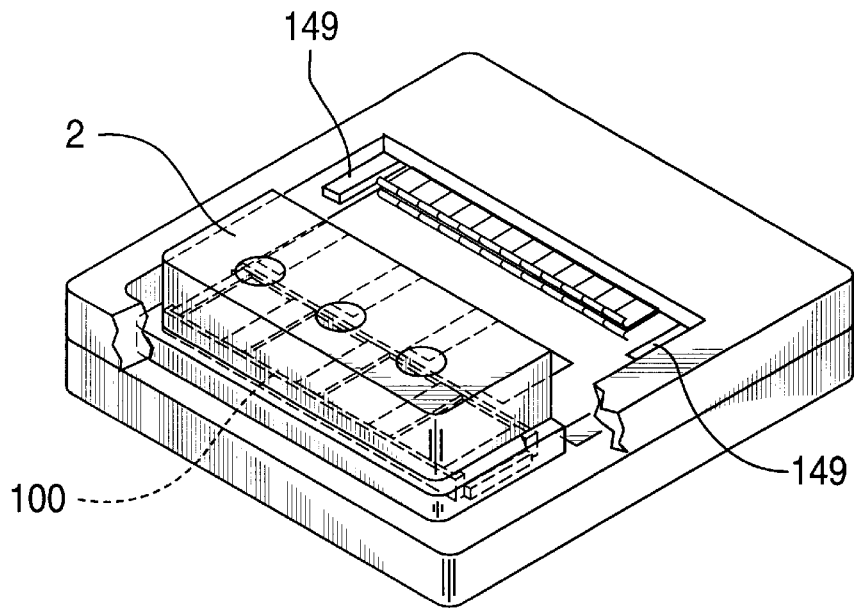
FIG. 10 is FIG. 9 modified in that the electrochemical sensor of FIGS. 1–7 covers the magnetic focussing device seen in FIG. 9.

In FIG. 10, there is an electrochemical sensor (2) covering the focussing device (100) shown in FIG. 9. The flat wing units (141) denoted in FIG. 10 are for holding the sensor in place when it is in the docking unit, especially when the platform and sensor are turned over in order to drain liquid from the cells of the sensor.

Figure 11:
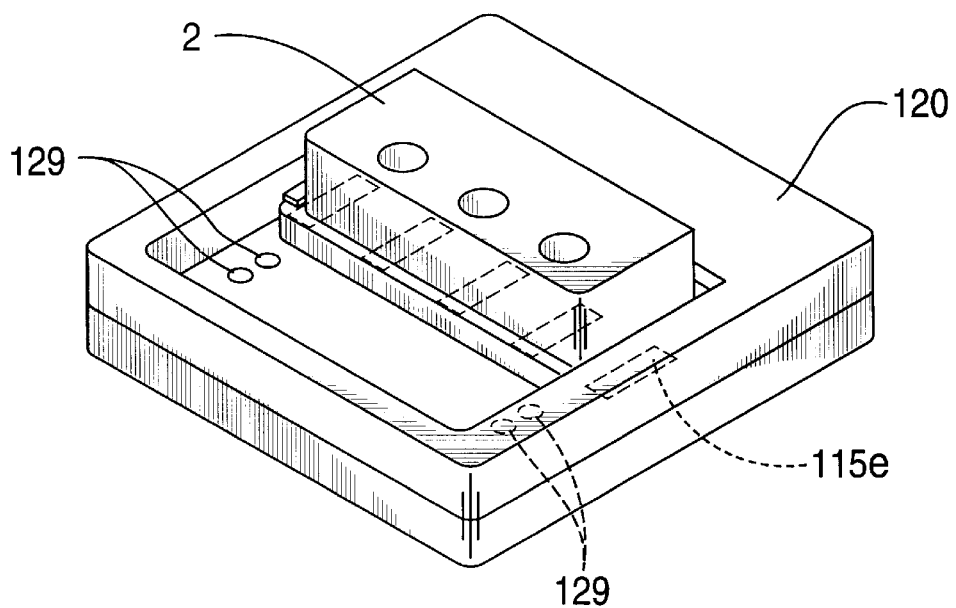
FIG. 11 is FIG. 1 modified to show the electrochemical sensor of FIGS. 1–7 after it has been slid into the docking unit on the platform; the magnetic focussing device seen in FIG. 9 is under the sensor and is hidden from view.

FIG. 11 shows a perspective view of the electrosensor unit (2) in the docking unit (120); the focussing device is within the lower portion of the electrosensor unit and is hidden from view. The sensor is directly over the magnetic field device. The rectangular top surfaces of the five pole-pieces of the magnetic field device are shown by dashed lines; one (115e) is denoted numerically. The electrosensor unit, together with the magnetic focussing device, can be slid from its position in FIG. 10 to its position in FIG. 11.

Figure 12:
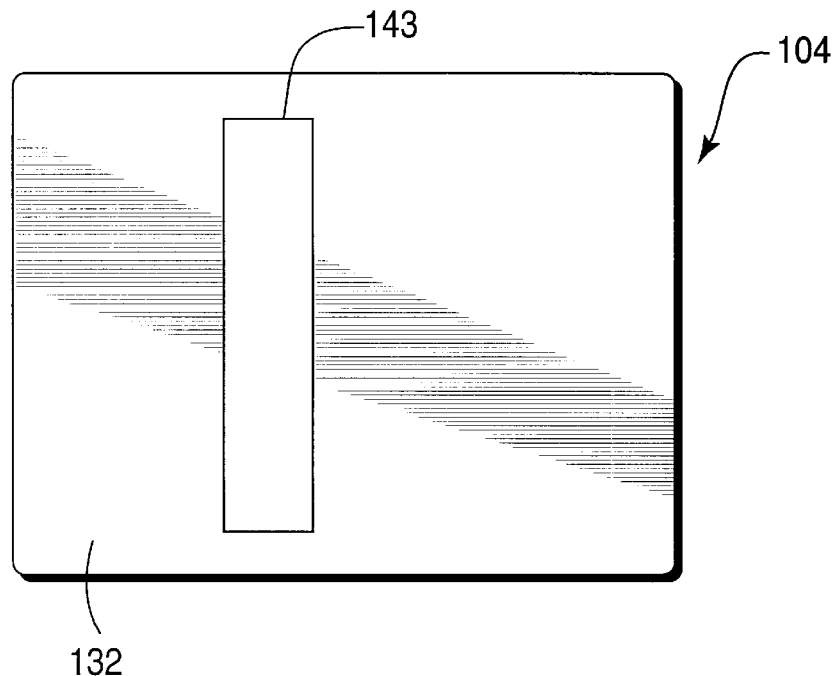
FIG. 12 is a bottom plan view of the platform unit shown in FIG. 8.

FIG. 12 is a bottom plan view of the platform unit (104) shown in FIG. 8 showing that unit's bottom surface (132). The rectangular area (143) is the surface of a block-shaped volume (157; shown in FIGS. 15 and 16) that can be made of a substance such as epoxy. The epoxy is added after the magnetic focussing device is inserted into the platform unit as part of the construction process of the unit. The rectangular surface (143) forms part of the bottom surface (132).

Figure 13:
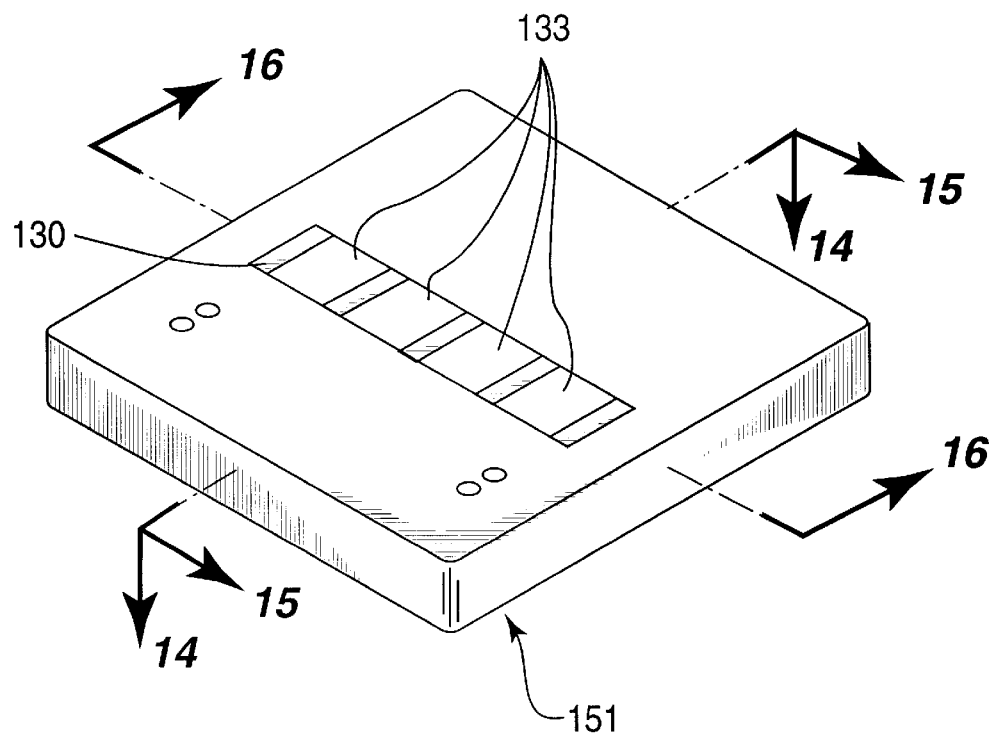
FIG. 13 is

FIG. 13 is a perspective view of the base (151) of the platform unit shown in FIG. 8. The magnetic field device, including its four rectangular cover units (133), are shown. The cover units were made of aluminum, the same substance of which the base unit was made.

Figure 14:
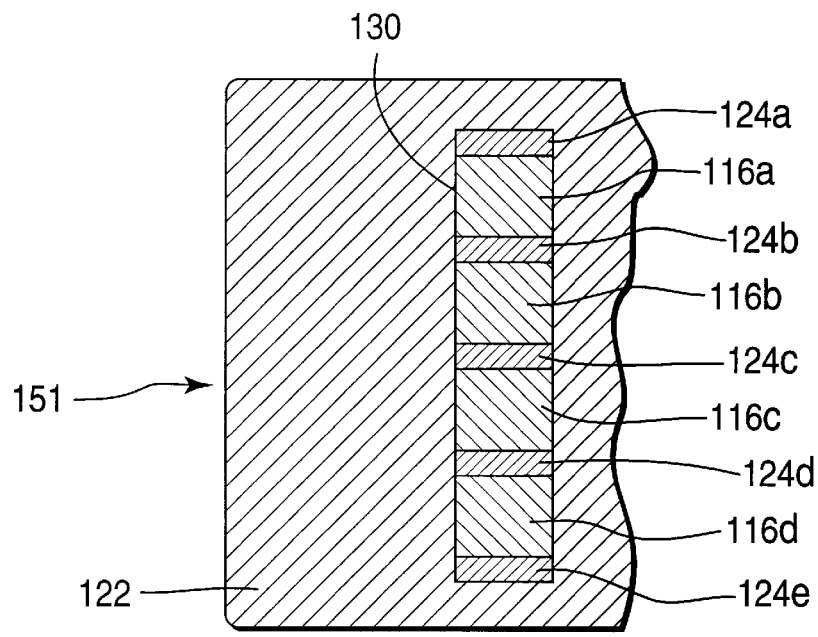
FIG. 14 is a cross-sectional view, taken along the 14—14 axis shown in FIG. 13.

FIG. 14 is a cross-sectional view taken along axis 14—14 shown in FIG. 13. FIG. 14 shows the magnetic field device (130) within the base (151) of the platform unit. The portion (122) of the base within which the magnetic field device is embedded is denoted. The five pole-pieces (124a–e) and the four magnetic structural elements (116a–d) are shown.

Figure 15:
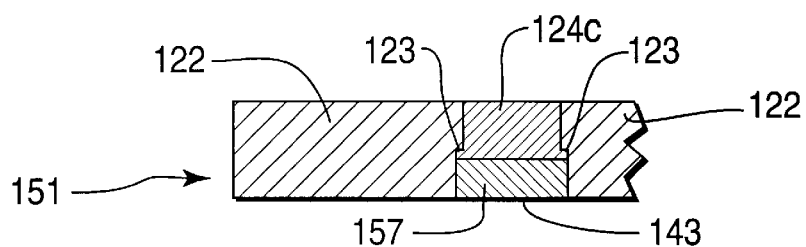
FIG. 15 is a cross-sectional view, taken along the 15—15 axis shown in FIG. 13.

FIG. 15 is a cross-sectional view taken along axis 15—15 shown in FIG. 13. The view shows the center pole-piece (124c) of the magnetic field device within the base (151) of the platform unit. Two small protrusions (123) of the center pole-piece are seen in cross-section. Also shown is the block-shaped volume (157) that was filled with epoxy.

Figure 16:
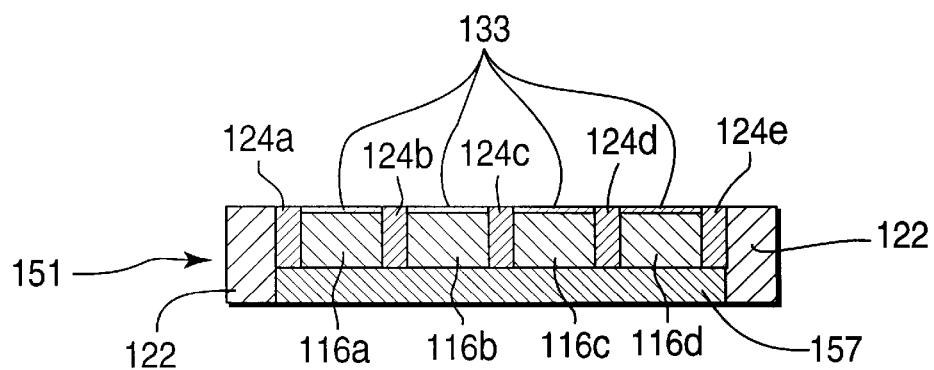
FIG. 16 is a cross-sectional view, taken along the 16—16 axis shown in FIG. 13.

FIG. 16 is a cross-sectional view taken along axis 16—16 shown in FIG. 13. The pole-pieces (124a–e) and magnetic structural elements (116a–d) that make up the magnetic field device are shown. Also shown is the block-shaped volume (157) that was filled with epoxy. Above each magnetic structural element is a thin cover unit (133).

Figure 17:
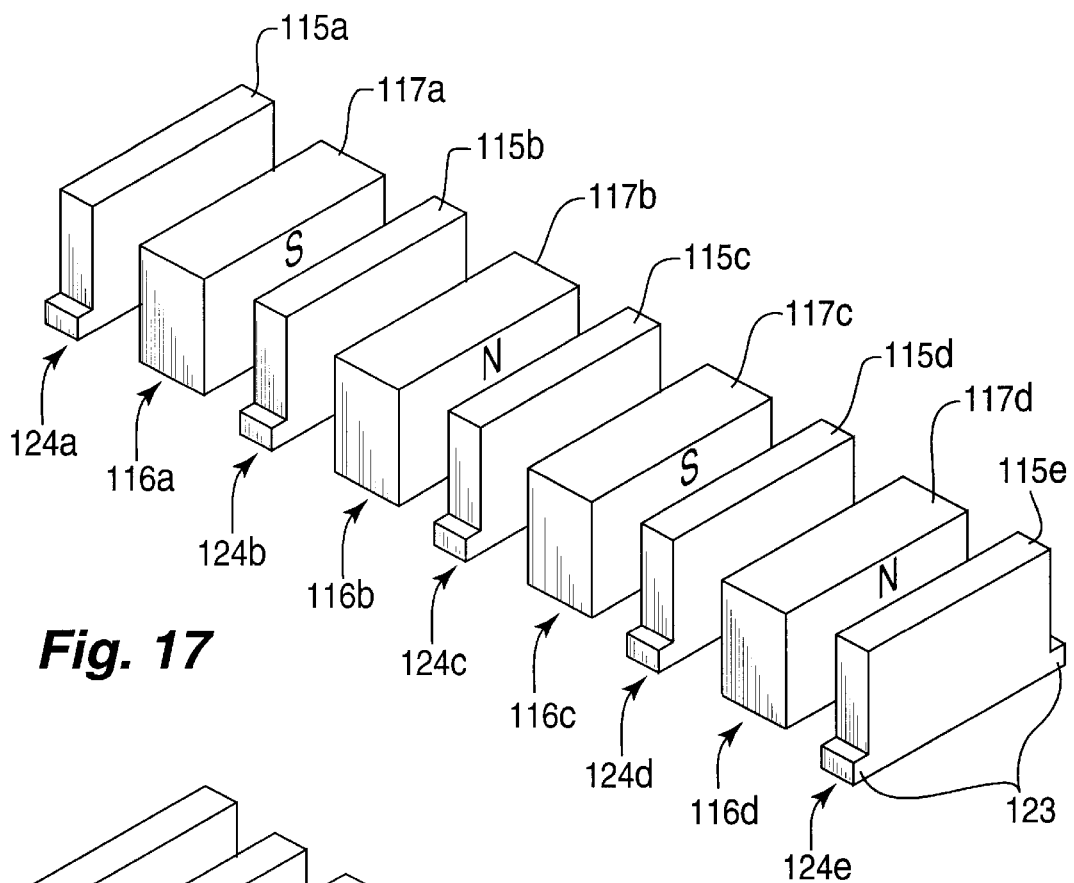
FIG. 17 is an exploded view of the magnetic field device embedded in the base unit of FIG. 13.

FIG. 17 shows an exploded view of the magnetic field device. The device is made of an array of five pole-pieces (124a–124e) and four magnetic structural elements (116a–116d). The top surfaces (115a–115e) of the pole-pieces and the top surfaces (117a–d) of the magnetic structural elements are denoted. The magnetic structural units are slightly shorter than the pole-pieces. As a result, when the structural elements are covered by cover units (133, see FIGS. 13 and 16) the tops of the cover units will be at the same level as the tops of the pole pieces (See FIGS. 13 and 16).

In FIG. 17, the North or South Pole of the magnetic structural elements are shown by the letters N and S, respectively, depending on which pole is on the face visible to the viewer of the Figure. It can be seen that any two successive magnetic structural elements in the array of four structural elements have opposite orientations as regards their polarity; therefore a pole-piece not at one of the two ends of the array will either (pole-pieces, 124b, 124d) be adjacent to the two South poles of two magnetic structural elements or (e.g., pole-piece 124c) adjacent to the two North poles of two magnetic structural elements.

Figure 18:
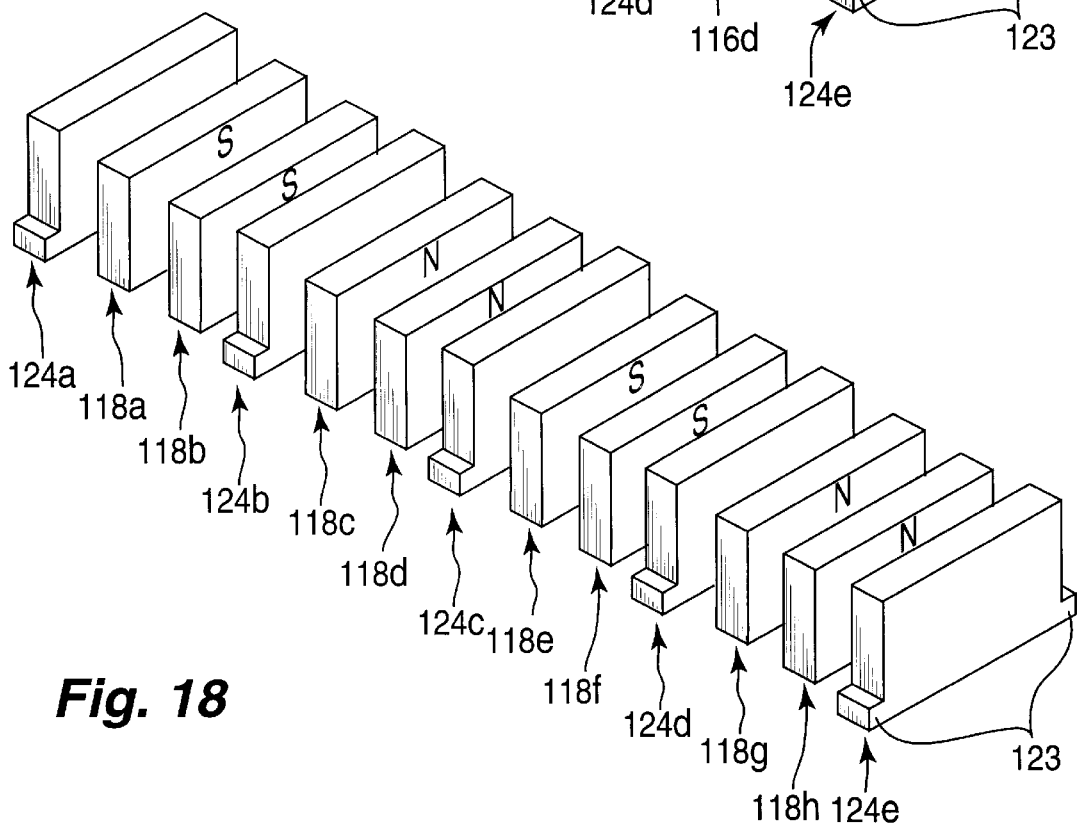
FIG. 18 is a further exploded view of the magnetic field device of FIG. 17.

Each magnetic structural element consists of two magnets, the device is further exploded in FIG. 18 to show the eight magnets (118a–118h) that make up the four magnetic structural elements. FIG. 18 also shows the five pole-pieces (124a–124e) shown in FIG. 17.

For the magnetic field device used in Example 2, the thickness of each pole-piece section as seen in FIG. 13 was 0.162 inches, and the thickness of each magnetic separator element was 0.372 inches, as a result, the length of device was 2.298 inches (5×0.162 inches+4×0.372 inches). The height each pole-piece was 0.264 inches.

In FIGS. 17 and 18, it can be seen that each pole-piece and structural unit has two small protrusions; for the end pole-piece (124e), in each Figure, the protrusions (123) are denoted numerically. The protrusions of the pole-pieces and structural units together create two rims along the magnetic field device, assisting in its positioning within the base unit of the platform.

In FIGS. 14, 17, and 18, it can be seen that the pole-pieces of the field device are in a linear array.

Figure 19:
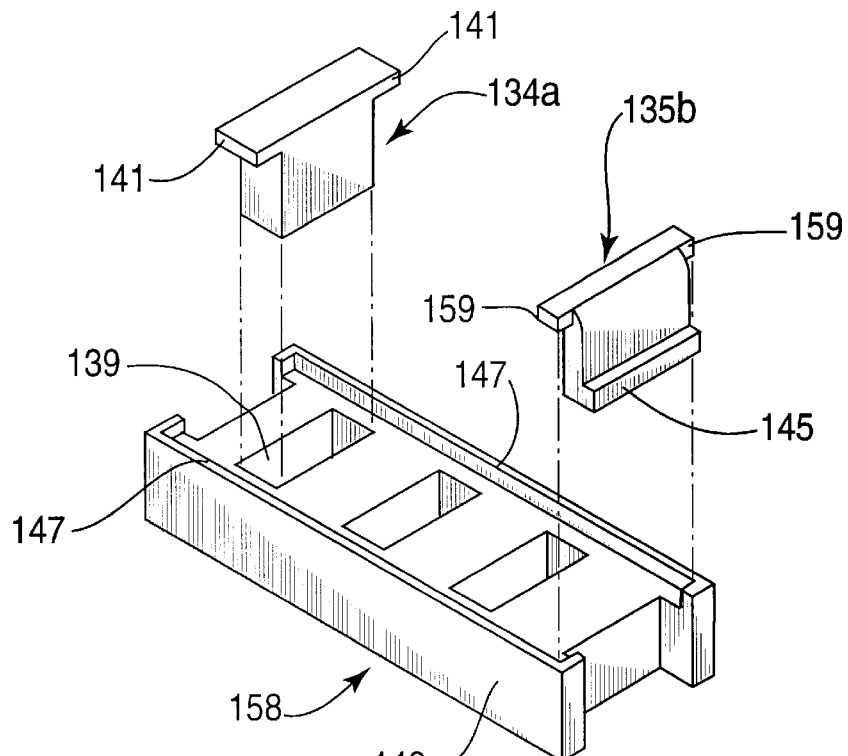
FIG. 19 is an exploded view showing selected components of the magnetic focussing device on the platform in FIG. 9.

FIG. 19 is an exploded view showing selected components of the magnetic focussing device: the nonmagnetic base block (158), one of the three internal pole-pieces (134) and one of the two end pole-pieces (135b). Three rectangular holes, one of which is denoted numerically (139), for receiving the internal pole-pieces are shown. Also shown are two rims (147) along the sides of the base block. It can be seen that the internal pole piece (134a) has two small wings (141). Similarly, the end pole piece has two small wings (159). The small wings rest on the top surface of the base block when the pole-pieces are in their proper positions in the magnetic focussing device. The end-pole piece also has a lower rim (145).

The milling of parts to create rectangular holes may necessitate the creation of small diameter channels at the point of intersection of the walls of the rectangle, in order to accommodate the drill bit used for milling.

The height of each side wall (142) of the non magnetic base block of the focussing device used in Example 2 was 0.215 inches; the length of each wall was 1.945 inches. The width of the base block was 0.66 inches. Where the base block contained holes (139) the width of the hole was 0.47 inches and its thickness was 0.142 inches of each rim. The span across the top surface of an internal pole piece (e.g., 134a) was 0.555 inches, reaching essentially from rim (147) to rim (147) of the base block. At its bottom, the thickness of each end pole-piece was 0.131 inches, just above the rim (145) it was 0.071 inches.

Figure 20:
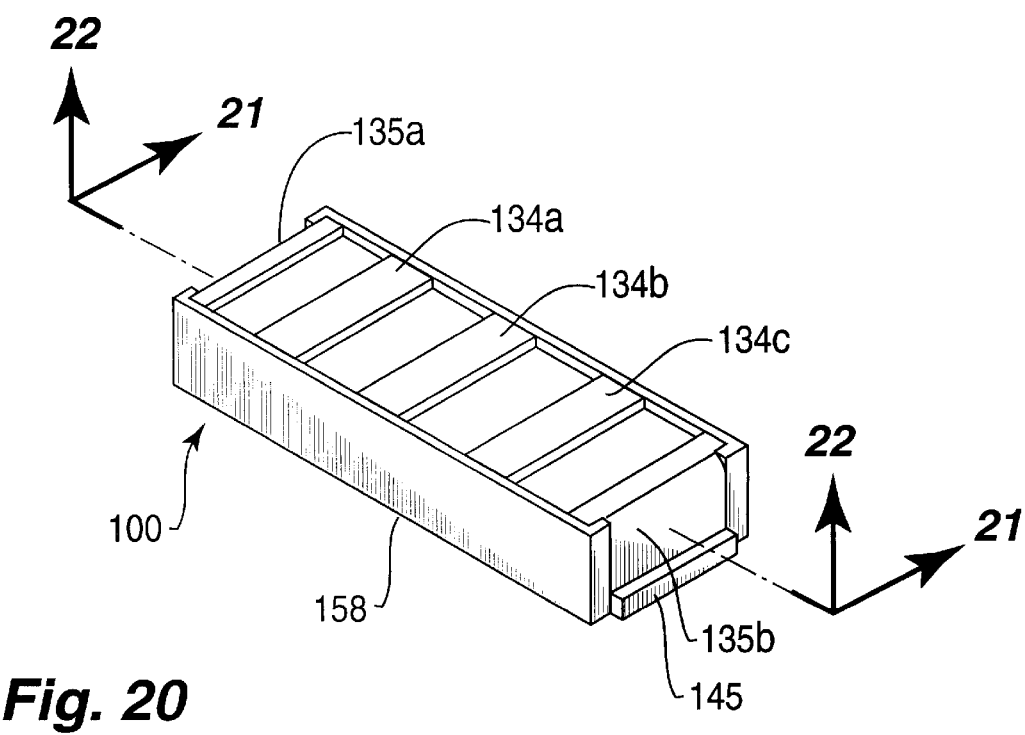
FIG. 20 is a perspective view of the magnetic focussing device shown in FIG. 9.

FIG. 20 is a perspective view of the magnetic focussing device (100) shown in FIG. 9 and, in part, in FIG. 19. The internal pole-pieces (134a–134c) and the end pole-pieces (135a–b), the lower rim (145) of an end piece, and the base block (158) are denoted.

Figure 21:
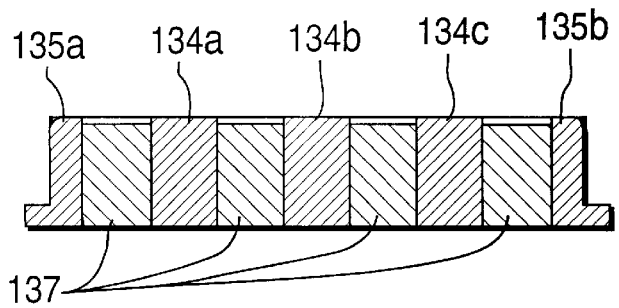
FIG. 21 is cross-sectional view of the magnetic focussing device taken along axis 21—21 in FIG. 20.
Figure 22:
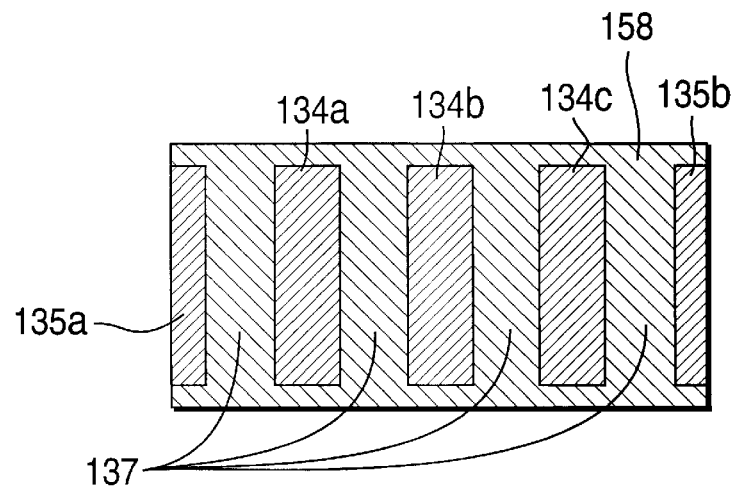
FIG. 22 is a cross-sectional view of the magnetic focussing device taken along axis 22—22 in FIG. 20.

FIGS. 21 and 22 are cross-sectional views of the magnetic focussing device of FIG. 20, taken along axes 21—21 and 22—22, respectively. In both FIG. 21 and 22, the end pole-pieces (135a–b) and the internal pole-pieces (134a–c) are shown. Also shown are the regions (137) of the base block (158) that separate the pole-pieces from each other, thereby functioning as non-magnetic separator elements.

In FIGS. 20 and 21, it can be seen that the pole-pieces of the focussing device are in a linear array.

Figure 23:
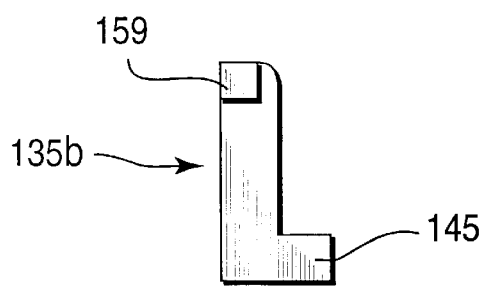
FIG. 23 is a side elevation view of the an end pole-piece shown in FIGS. 19 and 20.

FIG. 23 is a side elevational view of an end pole-piece (135b) of the magnetic field device. The wing (159) and the lower rim (145) of the pole-piece are denoted.

Figure 24:
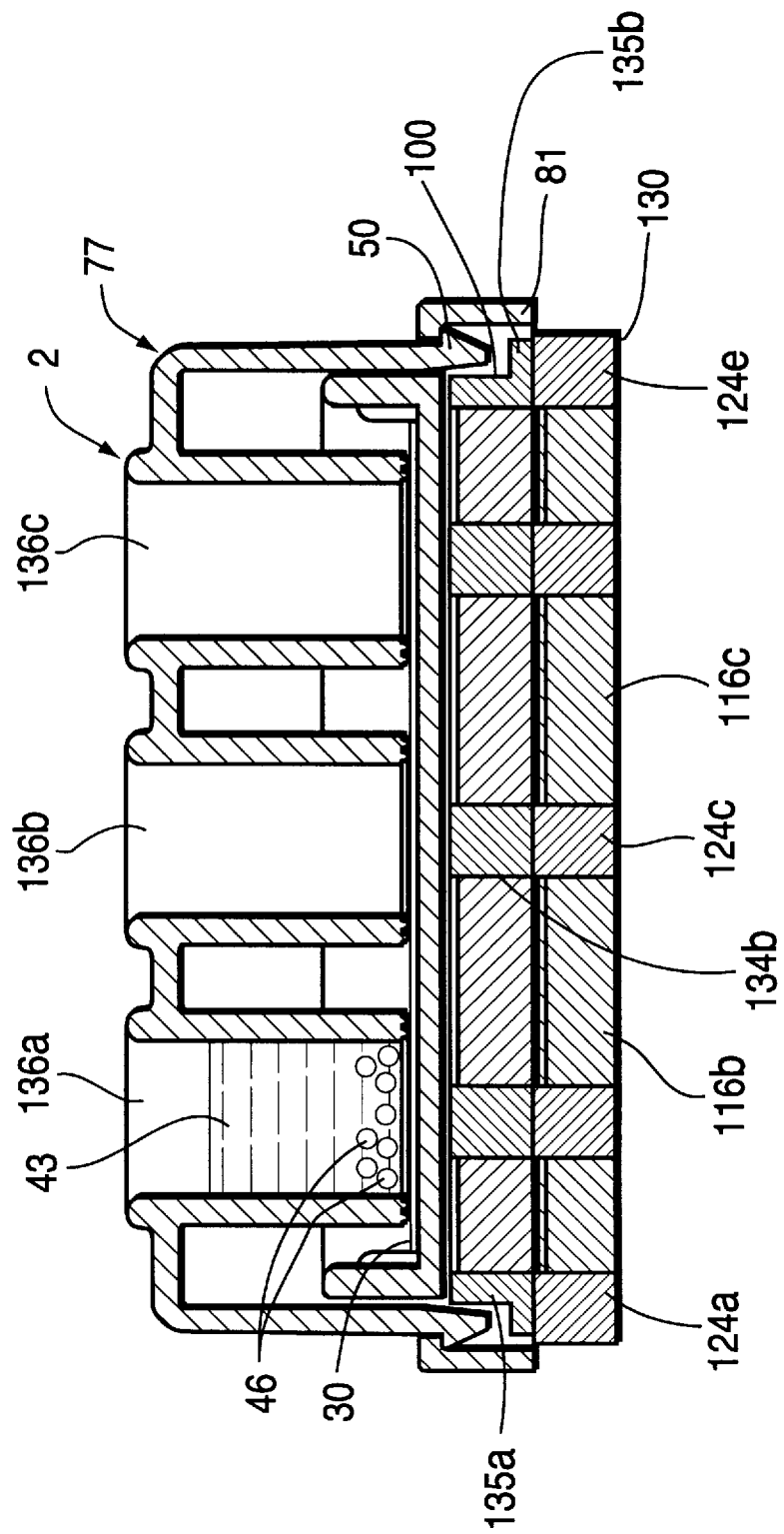
FIG. 24 is FIG. 4 modified to show the presence of the magnet focussing device and magnetic field device and their effect on the positions of the magnetic complexes.

FIG. 24 is FIG. 4 modified to schematically show how the magnetic focussing device (100) fits under the sensor (2) and the position of the magnetic field device (130) relative to the focussing device when the sensor and focussing device are directly over the field device as in FIG. 11. The cross-sectional views of the focussing device and the field device are the same as those shown in FIGS. 21 and 16, respectively. Three of the pole-pieces (124a, 124c, 124e) and two of the magnetic structural units (116b, 116c) of the magnetic field device are denoted. Three pole-pieces (135a, 134b, 135b) of the focussing device are denoted. The pole-pieces of the field device are aligned with both the pole-pieces of the focussing device and the sensor cells (136a, 136b, 136c).

As FIG. 24 is a cross-sectional view, it actually shows half of each cell. FIG. 24 shows the localizing effect the magnetic field device, in conjunction with the magnetic focussing device, has on the magnetic complexes.

Figure 25:
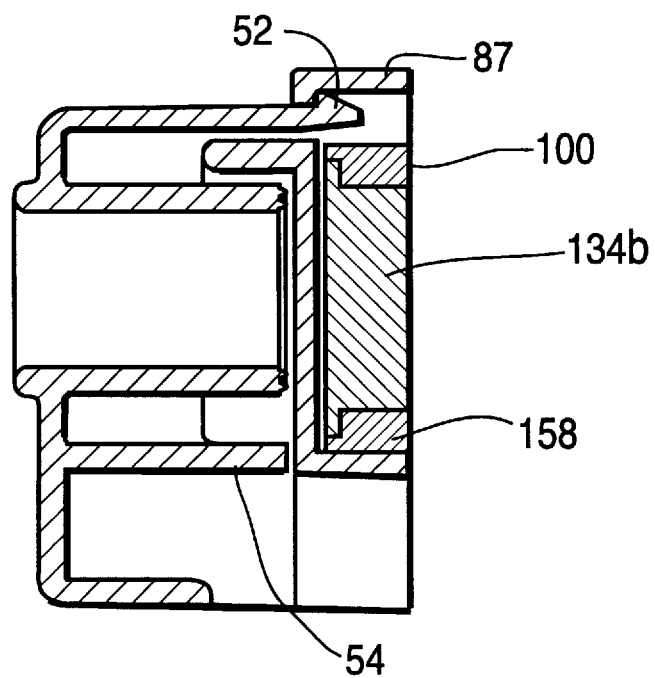
FIG. 25 is FIG. 5 modified to show the position of the magnetic focussing device when the device is present as in FIG. 22.

FIG. 25 is FIG. 5 modified to schematically show how the magnet focussing device (100) fits under the sensor.

DEPOSITION OF POLYMER ON THE ELECTRODE USED IN THE EXAMPLES

The electroconductive polymer was deposited onto a metallized polyester roll using a continuous gravure coating process that included heating to drive off excess solvent. The coated roll was then cut into appropriate size sheets. For deposition onto the polyester metallized sheet, a solution of 20 mg/ml polymer in toluene-xylene (85:15) was used.

FORMATION OF THE ELECTRODE ASSEMBLY USED IN THE EXAMPLES

The electrode assembly was made by first preparing a thin sheet (about 0.005 in. thick) of polyester (ICI-ST507 heat stabilized PET) with a silk-screen image of the desired line pattern comprising a water soluble paste, and then sputtering a platinum pattern on it.

Electrodes were fabricated by sputter-deposition of platinum to a thickness of approx 80 nm in high-vacuum onto polyester film rolls. The metal was pattern-defined using modified lithographic techniques in which a water soluble paste was applied to areas ultimately free of metal (in those areas, the metal will deposit on the paste instead of the polyester film), dried, and then after the deposition of metal, the paste was washed out along with its metal coating. This resulted in a parallel array of metal electrode strips and spacings. Electrode strip widths (0.68 cm) and spacings (0.05 cm) were patterned to be on-center with standard electrical connectors in an electronic instrumentation unit.

In a subsequent step in the assembly manufacturing process, the assembly was overlaid with a coating of poly (3-n-hexylthiophene) as described herein.

ELECTRONIC INSTRUMENTATION UNIT AND USER INTERFACE

An electronic instrumentation unit was used to measure changes in electronic current flow. An ac voltage (sine wave at 10 Hz) with a 200 mV peak was generated by a wave generator and applied to one electrode. Sensors were connected via their access electrodes to electrical connectors in the docking unit and thereby to an electronic instrumentation unit for measurement. An electrode connector of the docking unit scraped off the polymer from an access electrode surface during that electrodes' insertion into that connector. The output current, in the milliampere range, was converted to a millivolt value using a current-to-voltage converter. The change in output current (back-calculated from the millivolt output) was recorded as a function of time. In that way, the change in current as a function of time due to the creation of dopant in the cell was determined. Because the applied voltage is constant, the conductance or capacitance can be derived from the measured current.

The sensor with its magnetic focussing device inserted in its lower portion can be slid along the platform back and forth between positions such as those indicated in FIGS. 10–11. Guides may be added to the platform surface to assist positioning. A thin sheet of slippery plastic or lubricant may be added to the surface of the platform to assist removing the sensor and its magnetic focussing device from the attractive field of the magnetic field device in the platform.

EXAMPLES

Example 1

Detection of Atrazine

Magnetic components (Magnetic particles coupled to anti-atrazine antibody) were obtained from Ohmicron's RaPID Assays Division and are part of commercial kits sold by Ohmicron, Newtown, Pa. The magnetic components were concentrated by a factor of two, compared to their concentration in the stock solution in the kit, for this method. Atrazine-glucose oxidase conjugate was purchased from Biodesign (RR#2, Box 1048, Kennebunkport, Me. 04046).

Each sensor had three cells: to start the assay, 200 μl of the sample was added to the center cell and 200 μl of standard were added to each end cell. The assay was set up as if the critical concentration for distinguishing between a positive and a negative result was 2.5 ppb. For the assay, the known concentration of atrazine in both side cells was 2.5 ppb. The electronics were adjusted so that a response from a sample in the middle cell would be recorded as a positive result if it was less than or equal to the average response of the side cells and recorded as a negative result if it was greater than the average response of the side cells. This arrangement allowed samples of 3 ppb or greater to be recorded as a positive result 80 percent or more of the time. An aliquot of 200 μl of the concentrated magnetic components was pipetted into each cell and allowed to incubate with atrazine for one minute. Next, 50 ∥l of glucose oxidase-labelled atrazine conjugate were added to each cell and allowed to incubate for 4 minutes.

Conjugate buffer: 500 mM cacodylate, 20% glycerol; 10% ethanol; 1% BSA (bovine serum albumin); pH 6.0.

Magnetic Particle Buffer: 250 mM Tris, 150 mM NaCl, 1 mM EDTA, 0.1% BSA, 15 ppm Proclin 150, pH 7.4.

Development buffer: 500 mM cacodylate, 200 mM KI, pH 6.0.

10% glucose buffer: 500 mM cacodylate, 200 mM KI, 10% glucose, 15 ppm Proclin 150.

After the mixture had been incubated for at least 4 minutes but not more than 5 min, a magnetic field device was aligned under the cells. That device was different, however, than the one in the Figures and was bar-shaped to fit under the sensor just as the focussing device in the Figures herein was shaped. Furthermore, the device consisted of three disk-shaped magnets spaced to align with the sensor cells. The magnetic field device was used for one minute to pull the magnetic particles down to the electrode surface; the magnets remained in position until the end of the measurement.

After incubation, with the magnetic field device still keeping the magnetic components and complexes at the electrode surface, the sensor was turned upside-down to empty the solutions in the cells; keeping the sensor inverted, the top of the sensor was brought down with a rapid, vertical motion against absorbent towels spread on a table to blot excess solution.

Sensors were inserted into an electronic instrumentation unit and 200 μl of development buffer were pipetted into each well. A fixed a.c. voltage was applied to one electrode in each cell and the current was sampled through the other electrode. The reaction substrate (glucose) and other reagents needed so that the reporter conjugate if present would convert the reaction substrate to a dopant (triiodie) were added by adding 50 μl of 10% glucose-buffer to each cell to initiate the enzyme reaction. Triiodide, $I_3^-$ generated from the ensuing reaction caused a change in the electroconductive polymer film's impedance; the resulting change in current through the film was monitored electronically. The electronic instrumentation unit compared the response of the sample to the average of the standards and determined if the concentration of atrazine in the sample was greater (a positive) or less (a negative) than the average response of the standards.

Figure 27:
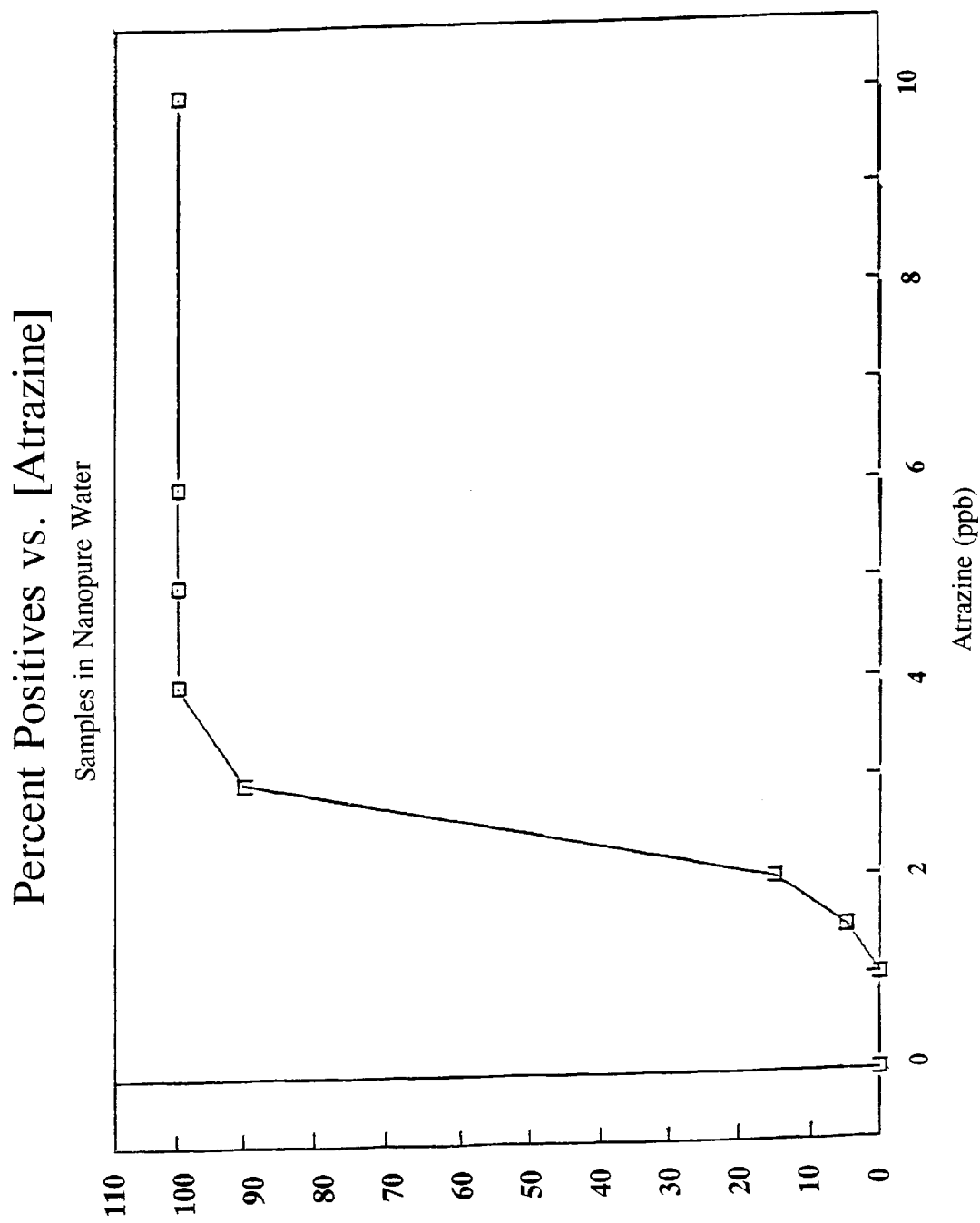
FIG. 27 shows the percent positive responses as a function of analyte concentration in the analysis described Example 1.

In one set of experiments, known amounts of atrazine were added to the solution in the center cell and, for each concentration of atrazine, the percent of positive samples was determined (FIG. 27). For each point on the graph in FIG. 27, 10–20 samples were tested. In FIG. 27, it can be seen that there were 10 percent false negatives when the concentration of atrazine in the test sample (center cell) was 3 ppb and none when that concentration was 4 ppb. There were 15 percent false positives when the concentration of atrazine in the test sample was 2 ppb and no false positives when that concentration was 1 ppb. The percentage of false negatives and false positives were sufficiently low that the assay was a useful one. (Similar results were obtained when the magnetic field device and magnetic focussing devices of the kind shown the FIGS. 8–25 were used.)

The usefulness of the assay was shown in a second set of experiments in which known amounts of atrazine (1.5 ppb or 3 ppb; 5 samples per test point) were added to samples from water sources from various locations (Table 1).

TABLE 1

| Water source | % Positive @ 1.5 ppb | % Positive at 3 ppb |
| --- | --- | --- |
| Allentown lake (filtered) | 20 | 80 |
| Coventry Cabin (well) | 0 | 80 |
| Newtown Tap | 0 | 80 |
| Ohmicron Stream | 0 | 100 |
| Tin House (well) | 0 | 100 |
| Wiedman (well) | 0 | 100 |

Example 2

Detection of Atrazine

A preferred procedure, and the one followed in this Example, is to run the competitive assay so that the order of addition is: sample containing the analyte, reporter conjugate, and magnetic complexes. Such a procedure allows the sample and conjugate to compete for antibody sites equally and, because the reporter conjugate is added with the conjugate buffer for the competition stage of the assay, it makes the system more tolerant of user timing and sample variability. The solutions used were the same as in Example 1, however the timing was altered to accommodate the order of addition.

A magnetic field device and a magnetic focussing device of the types illustrated in FIGS. 8–25 were used.

To start the assay, a 200 μl of aliquot of sample was added to the center cell of the sensor and 200 μl of standard were added to the two end cells. A quantity of 50 μl of conjugate buffer were then added to each cell; after all wells had received conjugate buffer, a quantity of 50 μl of magnetic complexes were added to each well. The solution containing the sample, reporter conjugate and conjugate buffer, and magnetic complexes were allowed to incubate for eight minutes. After incubation, a magnetic field was applied to the sensor for one minute to draw magnetic complexes to the electrode assembly surface. Following drawing the complexes to that surface, the solution was discarded, the electronic docking unit (already connected to the sensor) was connected to the electronic instrumentation unit, and the assay was continued as in Example 1, using development buffer and 10% glucose buffer to develop the assay response.

Figure 28:
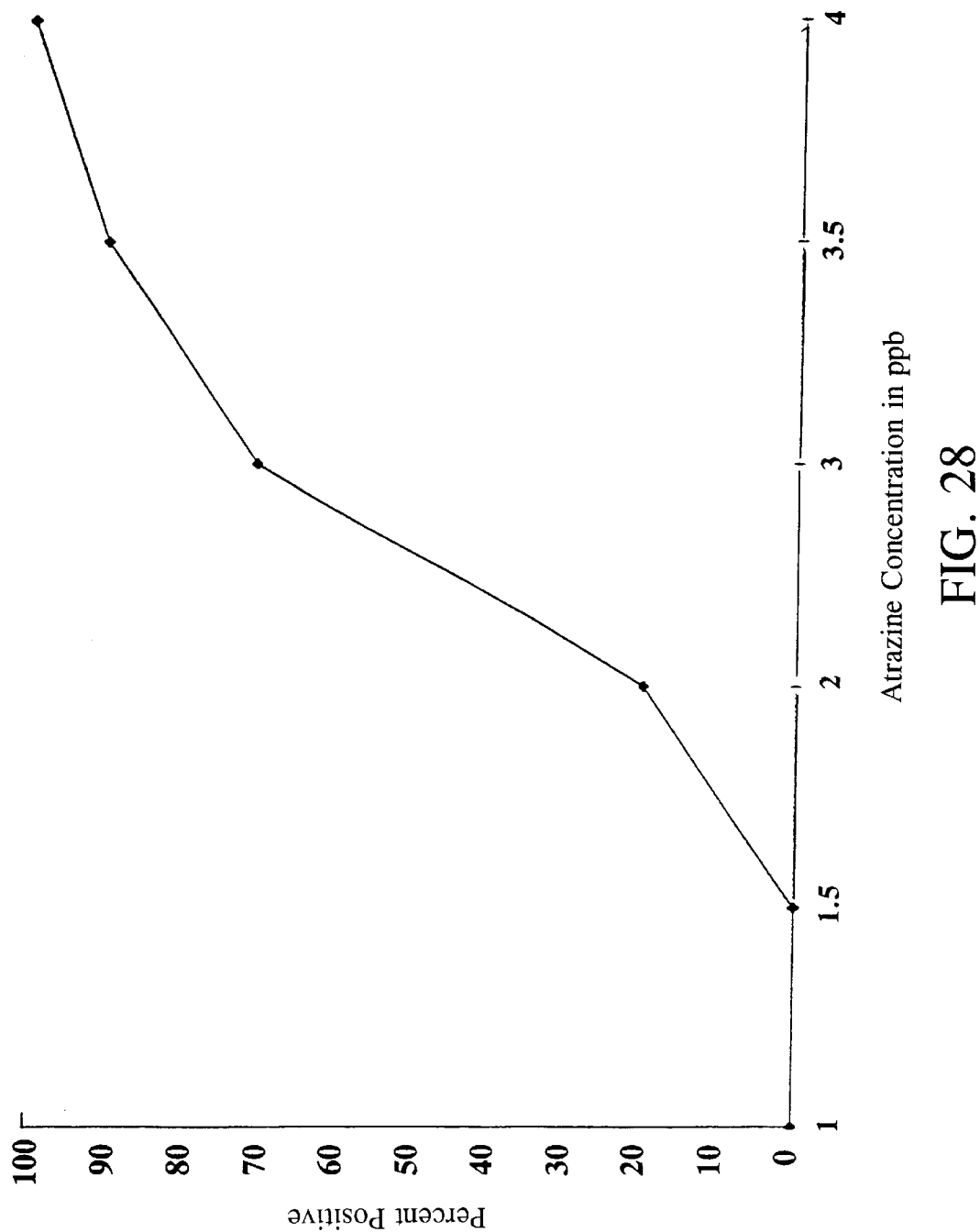
FIG. 28. shows the percent positive responses as a function on atrazine concentration in the analysis described in Example 2.

Results from the procedure are displayed in FIG. 28, which shows the percent positives of samples (relative to a decision level of 3 ppb). As shown by the data, this system yielded greater than 90% (true) positives above 3.5 ppb, less than 20% false positives at 2 ppb, and approaches 0% false positives below 1.5 ppb.

PART B

GRAVURE COATING PROCESS

Field of the Invention

The field of the invention are gravure processes for creating films of electroconductive polymers on solid surfaces.

Background

Thin uniform films of electroconductive polymers on flexible substrates are an important component of certain types of electronic sensors that detect and measure the concentration of chemical and biochemical compounds. Such sensors can be made by using electroconductive polymer films whose conductivity or capacitance changes when they are exposed to certain molecules, mechanical stress, or other factors. The response of a film to the molecule, stress, or other factor, depends in part on the thickness of the film. Many sensors have two or more wells for parallel processing of test samples and standard amounts of test compounds. Therefore there must be a degree of thickness uniformity sufficient to make meaningful comparisons between electrochemical measurements made at separated areas of the film in a sensor that accommodates multiple wells. Indeed, in many applications, it is desirable to have all the sensors in a large sensor lot have the essentially the same response to the molecule, stress, or other factor. As a result, although the size of the film used in each sensor tends to be small, it is economically important to be able to make large uniform sheets of film that can be cut into the small size pieces needed for each sensor. Otherwise, an excessive amount of time per sensor may be expended doing expensive quality controls. Indeed, in addition to uniformity, the large films must be non-blocking (pieces must not adhere to other surfaces they come in contact with) and be of an appropriate thickness that not only allows the film to withstand the physical demands of manipulation during the production process but also allows electronic responses that are linear in relation to the molecule, mechanical stress, or other factor, that changes its conductivity.

Methods that have been used to create electroconductive films are electropolymerization (Sato, U.S. Pat. No. 4,737, 557), dip-coating in a Langmuir-Blodgett bilayer system (T. A. Skotheim et al., *Thin Solid Films,* 178 233–242(1989)), pelletization (E. Pantka et al., *Mat. Res. Soc. Symp. Proc.* 247 753–758 (1992)), solvent casting (Y. Yoshino et al., *Jap. J. of Appl. Physics,* 28, 2027–2030 (1989)), spin coating (*Mat. Res. Soc. Symp. Proc.,* 293, 159–162 (1993).

In many instances, an organic solvent is required for the coating process. That requirement exists where (1) the polymer film is to be used in conjunction with an aqueous system assay and (2) the polymer must be formed prior to the film coating step. In such a case, the polymer cannot be water-soluble; otherwise it will dissolve from the film into the assay medium.

Of the above-noted procedures, spin coating is the preferred technique for depositing thin films onto flat and low profile substrates such as silicon wafers. For example, in such cases, polyimides may be dissolved in an organic solvent and a polyimide film may be generated by spin coating. With spin coating, the sensor surface area is typically very small and the film is very thin. A smaller and thinner electrode surface is well-suited as a substrate for a thin polymer coating. However, as the size of the surface increases, a point is reached at which the incidence of nonuniformity becomes too high to make spin-coating feasible. We have found that adequate uniformity can be obtained by spin-coating a solution of poly(3-n-hexylthiophene) in toluene with a rectangular Kapton sheet measuring 4.5 inches by 3.45 inches. That process required that spin-coating be uniform over a circular area, about 5.75 inches in diameter. As the size of that diameter is increased over 6 inches, however, it becomes difficult to control uniformity thickness because it is difficult to control the temperature, humidity, and evaporation rate, and keep the film contaminant free across the entire diameter. Limiting the process to diameters of 6 inches or less, means that in relation to the number of usable sensor films produced, an excessive amounts of equipment cost and personnel costs must be allocated to each spin-coating run.

The present invention utilizes a gravure coating process. Gravure coating processes are discussed by H. Benkreira in Thin Film Coating, The Proceedings of the Second International Symposium on Coating of Thin Films, pages 88–93 (1993), published by the Royal Society of Chemistry, Cambridge, England.

BRIEF SUMMARY OF THE INVENTION

In a general aspect the invention is continuous gravure coating process for forming a film of electroconductive polymer on the surface of a solid substrate, said process comprising, in the following sequence, the following steps:

(1) creating a solution comprising an electroconductive polymer dissolved in an organic solvent, (2) absorbing said solution directly onto the gravure surface of a cylinder, (3) transferring said solution from the gravure surface of the cylinder to a substrate surface, said surface being downwardly oriented, (4) evaporating the organic solvent from the solution transferred to the substrate surface so as to leave a film of the electroconductive polymer on the substrate surface.

BRIEF DESCRIPTION OF THE DRAWINGS

Figure 29:
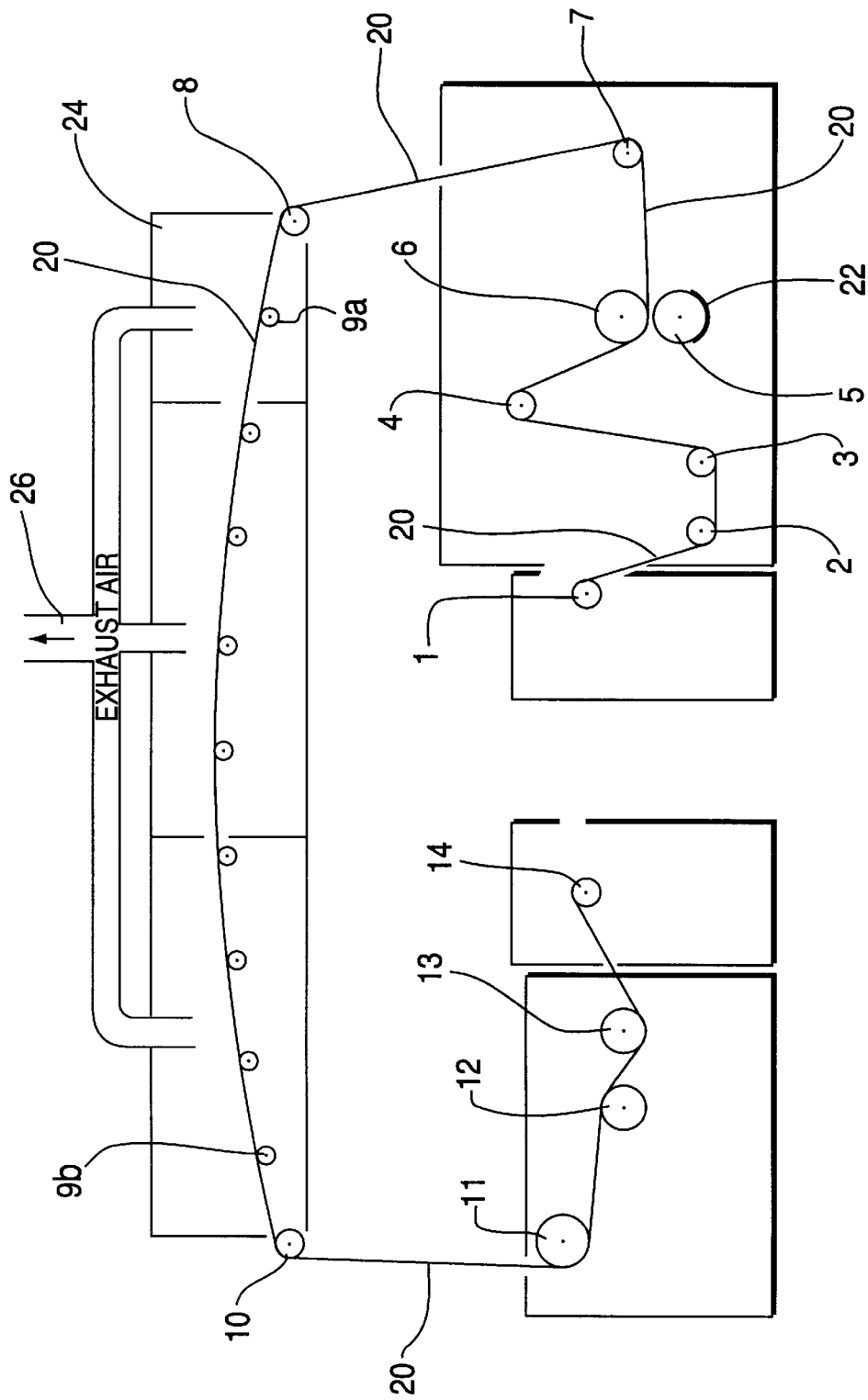

FIG. 29 is a schematic view of a large-scale coater.

Figure 30:
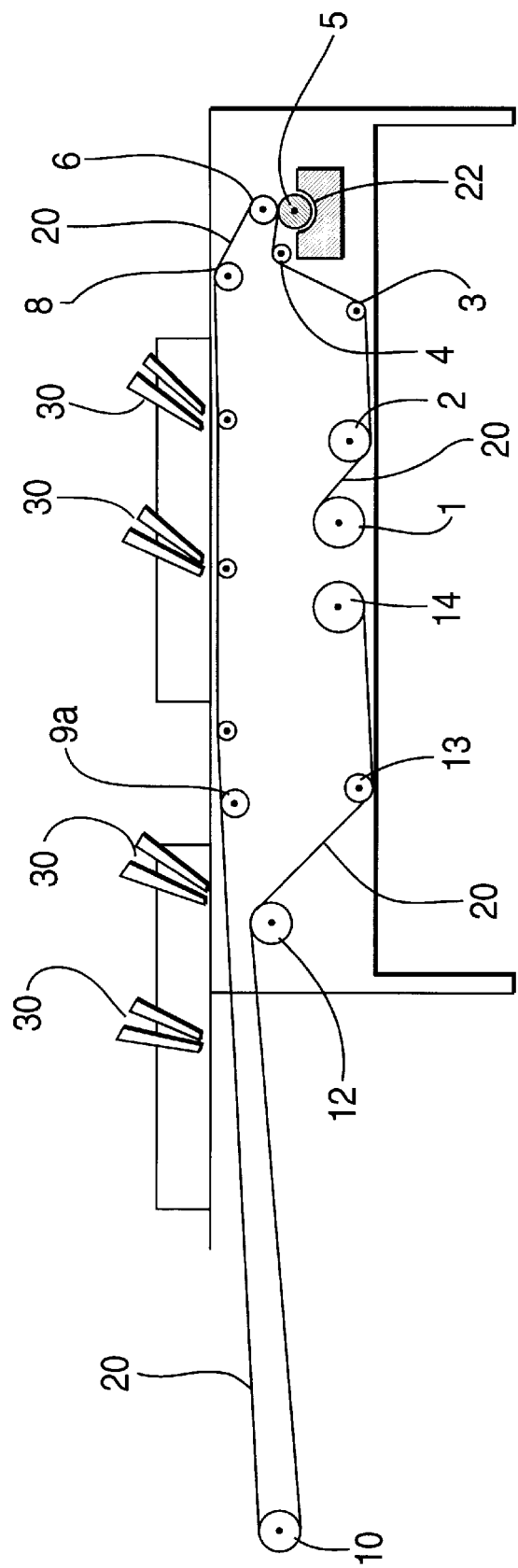

FIG. 30 is a schematic view of a small-scale coater.

Figure 31:
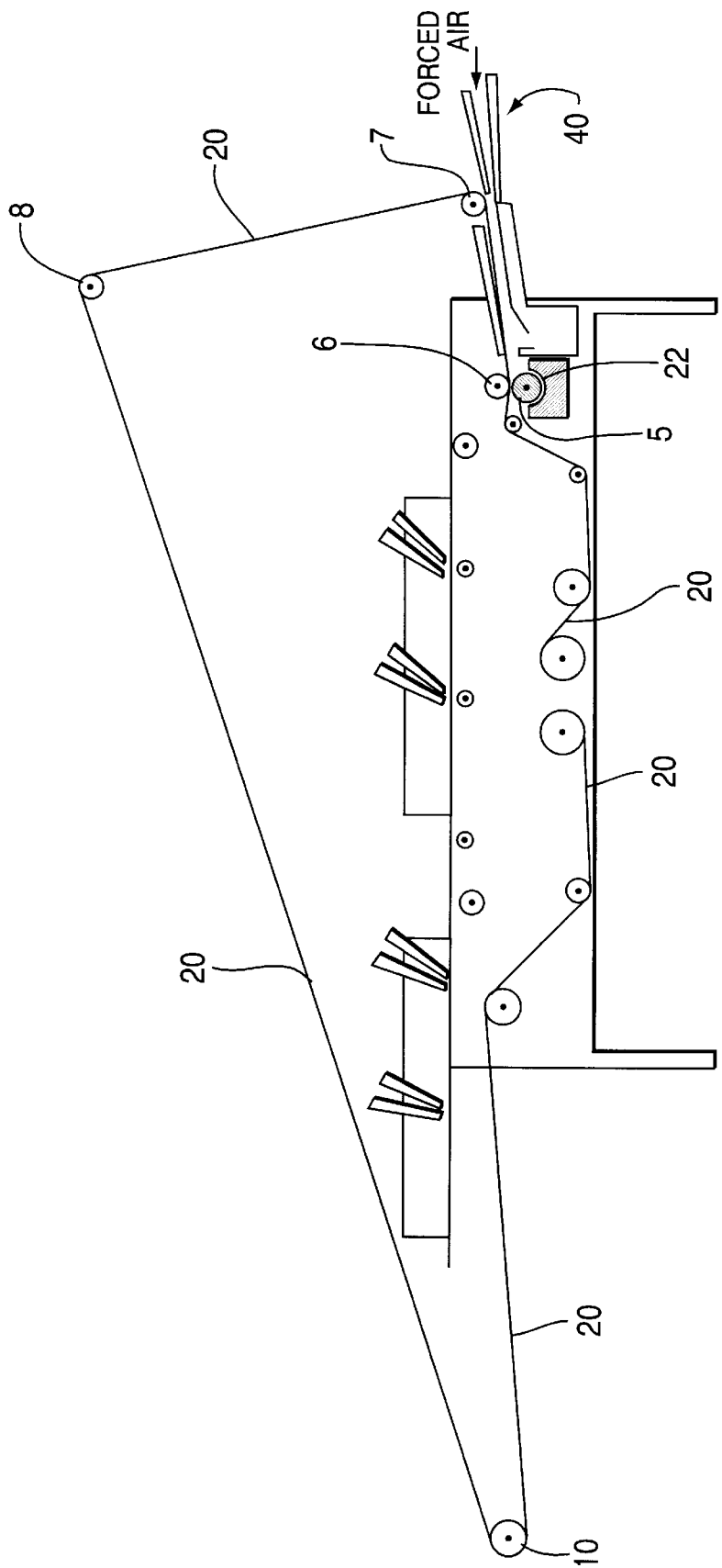

FIG. 31 is a schematic view of a modified version of the small-scale coater depicted in FIG. 30.

DETAILED DESCRIPTION

GLOSSARY AND DISCUSSION OF TERMS USED

An "electroconductive polymer" is a polymer whose conductance or capacitance can be changed by chemical oxidization or reduction, thermal excitation, optical excitation, or other physical excitation. Electroconductive polymers and their mechanism of action are disclosed and discussed by M. G. Kanatzidis et al, *Chemical & Engineering News,* Dec. 3, 1990, pp. 36–54. For sensors, oxidative doping converts an electroconductive polymer from a lower conducting to a higher conducting state. Reductive doping is also possible, however.

The spectrum of polymers that are electroconductive is very broad. They include, but are not limited to, polyacetylene, polypyrrole, polythiophene, poly(3-alkylthiophene), polyphenylene sulfide, polyphenylene vinylene, polythienylene vinylene, polyphenylene, polyisothianaphthene, polyazulene, polyfuran, polyaniline, and derivatives of the foregoing.

"Dopants" are molecular species that react with an electroconductive polymer so as to change the conductivity of that polymer. Examples of dopants include, but are not limited to, $I_3^-$, $BF_4^-$, $ClO_4^-$, $FeCl_4^-$, $NOPF_6^-$, and $N_2H_4$.

An "electroconductive sensing element" is part of a sensor whose electrical properties change in response to the presence of an analyte. The change may be due to the analyte interacting directly with the sensing element or due to the analyte triggering the production or diminution of a substance that interacts directly with the sensing element. Examples of sensing elements are those made of metal and those made of electroconductive polymers.

An "analyte" is a substance that an analytical procedure seeks to detect and quantify. Some analytes (e.g., $Na^+$) can interact directly with a sensing element and cause detectable changes in that sensing element's electrical properties. Some analytes can be detected because they trigger or inhibit chemical or biochemical reactions that generate dopants (e.g., $I_3^-$) that affect the electrical properties of sensing elements.

"Drying means" is a means for accelerating the evaporation of a solvent from the surface of the substrate and includes an oven, an air blower or fan, a heating element, a vacuum creation system, and the like.

A sheet that is horizontally disposed will have a top surface that is "upwardly oriented" and a surface, on the underside of the sheet, that is "downwardly oriented". An "organic solvent" for use in the present inventions is one that comprises carbon atoms as part of its molecular make-up and which is at least partially not miscible with water but into which an electroconductive polymer of interest for use in the processes of the present invention can be dissolved.

A "gravure roll coater" is a roller, normally metal, whose surface is characterized by a regular arrangement of precisely defined cavities created by chemical or mechanical engraving. Typical arrangements are categorized as quadrangular, trihelical, or pyramidal. (See H. Benkreira, above). In the present examples, a quadrangular arrangement was used.

In a "direct" gravure coating process, a coating solution is transferred directly to the surface to be coated. In an "indirect" gravure coating process, the coating solution is first transferred from a gravure to a second roller, such as a rubber roller, which second roller then transfers the coating solution to the surface to be coated.

A "polymer", in the case of a homopolymer, is considered to be any molecular chain where the repeating unit is present at least 20 times (i.e., the degree of polymerization is at least 20.) In cases where the polymer is a copolymer, each unit in the chain is counted once independent of its identity, so that for example the degree of polymerization with 10 monomers of type A and 10 monomers of type B is 20.

"Blocking" refers to the phenomenon whereby a polymer film on a first sheet substrate is brought into contact with a polymer-free surface of a second sheet and, as a result, there is transfer of one or more blocks of film from the first sheet substrate to the second one.

The invention

The present invention achieves the goal of producing large uniform, nonblocking electroconductive polymer films of desired thickness on a solid substrate in an economical manner. The invention achieves its goal by using a direct gravure coating process in combination with a continuously fed substrate; the process is enhanced when air is moved over the substrate in a direction counter to substrate motion soon or immediately after the substrate is coated on its downwardly oriented side with solution containing the polymer.

In the gravure process, a solution of the polymer is transferred from a gravure roll to the substrate; the substrate must then be dried so as to evaporate the solvent and leave a polymer film on the substrate. In one important embodiment of the process, a drying oven is at a height greater than that of the gravure roll. In that embodiment, the substrate goes through a vertical orientation phase prior to the time the solvent has been fully evaporated. Prior to the present invention being successfully carried out, it was not obvious that the polymer solution would not run down the surface of the substrate under gravity so as to cause such nonuniformity of thickness as to preclude meaningful comparisons between electrochemical measurements made at separated areas on a film in the same sensor (e.g, one area used for a well with an sample having an unknown amount of analyte, another area or two areas used with known amount of analyte in the assay). Indeed, this was considered a risk generally for solutions with a viscosity of less than 100 cps and a particularly great risk considering the low viscosity of the polymer solutions, about 4 cps or less, frequently used with poly(3-n-hexylthiophene). Furthermore, the problem was not necessarily avoidable by merely increasing the concentration of the polymer in the solvent so that one can correspondingly decrease the thickness of the applied polymer solution. Many electroconductive polymers are only soluble at low concentrations in organic solvents.

In the gravure roll process of this invention, the substrate is coated on its underside with polymer solution before it, the substrate, moves into a vertical orientation phase. Even for the embodiment where the substrate is not in a vertical orientation phase prior to being fully dried, however, prior to the invention being successfully carried out, it was not obvious that there would be uniformity of film thickness given the low viscosity of the solution being coated. The risk prior to the completion of the invention was running and drippage from the underside of the substrate might occur and, combined with the large area of substrate being used, nonuniformity of film thickness would be created by local fluctuations in temperature, humidity, and mechanical agitation during the drying process.

In a general aspect the invention is continuous gravure coating process for forming a film of electroconductive polymer on the surface of a solid substrate, said process comprising, in the following sequence, the following steps:

(1) creating a solution comprising an electroconductive polymer dissolved in an organic solvent, (2) absorbing said solution onto the gravure surface of a cylinder, (3) transferring said solution directly from the gravure surface of the cylinder to a substrate surface, said surface being downwardly oriented, (4) evaporating the organic solvent from the solution transferred to the substrate surface so as to leave a film of the electroconductive polymer on the substrate surface.

Usually, the substrate will be a flexible substrate. However, it is possible to transfer the coating solution to a nonflexible substrate, such as glass. A nonflexible is treated the same as a flexible one, except that it cannot be rolled up.

The process in its most preferred mode is done under conditions that have no or almost no nonuniformity (evidenced by chatter lines, substrate tension lines, and fisheyes). Evidence for nonuniformity can be visual if the polymer has a color. Nonuniformity within a specified area is then evidenced by variations in color, in the darkness of the color, in the brightness of the color, or in a similar aspect of the color intensity. If the polymer does not have a color, a test for nonuniformity is ellipsometry or profilometry.

It is preferred that step (4) be accelerated by applying a drying means to evaporate the solvent. If after step (3) is completed and before step (4) is completed, the substrate is in a vertical orientation phase, it is preferred that two drying means be applied: a first drying means is applied after step (3) is completed and prior to the time that the substrate surface has a vertical orientation; a second drying means is applied after the time the substrate surface is in the vertical phase. The first drying means most preferably accomplishes sufficient drying so that fish-eyes and other nonuniformities do not occur prior to application of the second drying means. The second drying means completes any uncompleted evaporation of the solvent from the substrate surface and also makes the film firmer than it otherwise (in the absence of the second drying means) would be. In the case of the present films, poly(3-n-hexylthiophene) a temperature over 160° F. is desirable to achieve firming, a temperature under of about 200° F. or less is desirable to avoid deformation of the polyester substrate.

The substrate will normally be a flexible sheet.

Electroconductive Polymers

The spectrum of polymers that are electroconductive is very broad. They include, but are not limited to, polyacetylene, polypyrrole, polythiophene, poly(3-alkylthiophene), polyphenylene sulfide, polyphenylene vinylene, polythienylene vinylene, polyphenylene, polyisothianaphthene, polyazulene, polyfuran, polyaniline, and derivatives of the foregoing in which a repeating unit is substituted, for example poly(3-n-hexylthiophene). Substitution groups for such derivatives include polymers of alkyl (especially alkyl of 1 to 12 carbons), alkoxy (especially alkoxy of 1 to 3 carbons), cyclopentyl, cyclohexyl, benzyl, acetyl, p-tolyl, furyl, phenyl, and halo (chloro, bromo, iodo).

Polymers of particular interest are polythiophene and its derivatives, especially polymer of alkylthiophene where the alkyl group has 1 to 12 carbons. An electroconductive polymer of particular interest is one that, with at least one of the dopants, $I_3^-$, $BF_4^-$, $ClO_4^-$, $FeCl_4^-$, $NOPF_6^-$, $N_2H_4$ or protons, has a conductivity of at least 1 Siemens/cm when fully doped.

Polymer Concentration

The polymer concentration may be as high as needed provided that the solution is not too viscous to prevent uniform transfer of solution from the gravure roll across the substrate.

Solvent(s)

Any organic solvent in can be used as long as the polymer is soluble in the solvent and the solvent does not damage the polymer.

Among the solvents that will be most commonly used are chloroform, toluene, xylene, tetrahydrofuran, methylene chloride, and tetrahydronaphthalene.

Solvent combinations of two or more of the above are usable.

Substrate Composition

The substrate can be any substrate with a surface for which the solvent has sufficient attraction so that the surface tension of the solvent does not prevent the solvent from spreading uniformly over the substrate surface. Preferred substrates are hard, flexible organic solids such as plastics. Preferred plastics are those with polyimide, polyester, or polycarbonate; however, a wide range of plastics can be used. In many cases, the surface will be metallized: partly or completely covered with a thin layer of metal (such as by sputtering or evaporating). Uniformity of film thickness is enhanced by plasma-cleaning the surface to be coated.

Oven Temperature and Time

The oven normally is heated to temperatures as high as possible providing the temperature is not so high as to damage with the sheet or the polymer film. For poly(3-n-hexylthiophene) on polyester, for example, oven temperatures of 78° C. to 95° C. were used successfully to achieve solvent evaporation. (See discussion for Example 4. Residence time at 95° C. in the oven ranged from 45 sec to 120 sec for successfully drying toluenelxylene (85/15, v/v) solution or a toluene/xylene/indan (85/10/5, v/v/v) ratio. However, a variety of shorter or longer residence times, although untested, would also be expected to be successful. Due to the potential fragility of the coated surface, there was prior to the completion of the invention great concern that blocking of the polymer would occur if the coated film was self-wound. In fact, despite the short residence time in the oven, if the film was coated to a sufficiently high temperature, blocking was not a problem. Nonetheless, the film is sheeted and interleaved with an inert liner soon after coating.

The oven residence time can be whatever is required to desolvate the polymer solution so that the coating is firm, nontacky (not sticky to the touch), and will not block onto the substrate.

Use of Coated Substrates in Sensors

A three-well cartridge-type sensor that can utilize a thin metallized substrate coated with a thin film of an electroconductive polymer was described in PCT application number PCTIUS94/02010 of Ohmicron Technology, Inc.

The use of sensors for detecting analytes has been disclosed in U.S. Pat. Nos. 4,560,534 (Kung et al.), 4,929,313 (Wrighton et al.), and 4,334,880 (Malmros et al.). It has also been disclosed in European patent documents 193154 (Taniguchi et al.), 467219A2 (Musho et al.), and 314009 (Arabella et al.) as well as numerous other publications and patents. The aforementioned patent publications specifically discuss the use of antibodies on an internal surface of a cell (Malmros, Taniguchi), the use of an enzyme on a cell surface (Arabella), the detection of small ions ($H^+$, $Li^+$, and others, Wrighton) and enzymatic reactions that generate the dopant, $I_3^-$ (Musho).

EXAMPLES

Apparatuses used in the Examples below

Tests and demonstrations of functionality were done on two types of apparatus, arbitrarily referred to as a large-scale apparatus and a small scale apparatus. Each are considered to be illustrative of the type of apparatus used to perform the processes of the invention, but not the only types of apparatus that can be used for that purpose.

The large-scale apparatus is shown in FIG. 30. The apparatus had an unwind role (1) which was the source of the substrate (20) that was wound around the unwind role. The substrate passed over a first directional roll (2) used to adjust the direction in which the substrate moved off the unwind roll. Next, the substrate, still free of polymer solution or film, passed over a second directional roll (3) before entering a vertical mode of movement. It then passed over a third directional roll (4) which turned its direction downward. The next roll encountered by the substrate was a nip roll (6) with a rubber surface. As the substrate passed over the nip roll, it was pressed against the gravure roll (5) (pressure was created by air cylinder-generated air from above on the rubber nip roll (6)). At that point, the gravure roll transferred a polymer solution to the downwardly oriented side of the substrate. The polymer solution was present in a trough (22) to which it was continuously fed by a dropping funnel. (The surface of the gravure roll was wiped by a blade, not shown, as it left the trough.) The substrate then traveled through a horizontal mode followed by contact with a fourth directional roll (7). The fourth directional roll turned the substrate, with polymer solution on its surface, into a vertical orientation phase. The degree of vertical orientation in the vertical orientation phase is equal to the angle between the substrate and the horizontal. That angle can vary from just greater than zero degrees to 90 degrees; in the case of the commercial coater, it was about 80 degrees. The coated substrate then came in contact with a fifth directional roll (8) that turned it into a substantially horizontal mode for passage through a drying oven (24). The drying oven had a series of support rolls (six to fifteen) of which the first (9a) and last (9b) are denoted. As the substrate passed through the drying oven, any residual solvent in which the polymer was dissolved evaporated. Drying was assisted by an exhaust system (26). At the exit point of the oven, there was a sixth directional roll (10) which turned the substrate into a downward direction. The substrate then encountered a seventh directional roll (11) which turned the substrate into a horizonal mode. A main drive roll (12), preferably with a foam cover and driven by a motor, pulled the substrate along while pressing against the film-coated side of the substrate, it was the main driving force for propagating the substrate through the process. The substrate then came into contact with a second drive roll (13) before finally coming in contact with a windup roll (14). The rate of the two drive rolls was controlled by two tensiometers (each sensing the pressure on a roll as in indicator of tension in the substrate), one that sensed the tension in the substrate prior to substrate entry into the oven and one that sensed the tension in the substrate after the substrate exited the oven.

The gravure roll (5) had a 120 Q cell size in contact with a hard rubber backing roll. The processes of the current invention can, however, be carried out with other cell sizes. The cell size, which controls the amount of solution transferred per square inch of substrate, and the polymer concentration in the polymer solution determine the final weight of polymer per square inch of polymer film (the "coating weight"). For example, a smaller cell size gravure and a higher polymer concentration in the solution can produce the same coating weight as a larger cell size gravure and a lower polymer concentration in the solution.

The gravure pattern on the large scale coater was a quadrangular pattern utilizing a cell size of 120 Q, each cell with an area of $3.92 \times 10^{-4}$ $cm^2$, a depth of 120 microns ($1.2 \times 10^{-2}$ cm), and a volume per cell of $28.5 \times 10^{-9}$ cubic million microns.

The gravure pattern on the small scale coater was a quadrangular pattern utilizing a cell size of 110 Q, each cell with an area of $4.84 \times 10^{-4}$ $cm^2$, a depth of 98 microns ($0.98 \times 10^{-2}$ cm), and a volume per cell of $25.5 \times 10^{-9}$ cubic million microns.

The small scale apparatus had essentially the same elements as the large scale apparatus except that it did not have the fourth (7) and seventh (11) directional rolls, and had an air dryer (blower) instead of an oven. Tension on the substrate after the gravure nip roll is not provided by main drive rolls (12) and (13) as is the case in the large scale coater but is supplied by the windup roll (14). The blower (not shown) blew air into a manifold (not shown) that directed the air through four air bars (30) from which it blew unto the coated substrate surface. The gravure roll (5) was not a drive roll. Pressure was created between the gravure roll and the substrate surface by means of a counterweight arrangement (not shown) that pushed the gravure roll in an upward direction. The rolls (6), (8), (9a), and (13) were connected by a timing belt (not shown in FIG. 30). The main drive was connected to the nip roll (6), the unwind roll (1) was connected to an unwind tensioner (not shown), and generally it had smaller dimensions (See Table 1). Each air dryer had a 3000 rpm air moving unit that operated on ⅛ of a horsepower and blew air threw four slots whose areas totalled together 1.5 square inches. At the end of each run in the small scale coater, the coated substrate was moved to an oven and baked at 90° C. for 15 minutes.

TABLE 1

Dimensions

|  | large scale coater | small scale coater |
|---|---|---|
| diameter, unwind roll (1) | 3 inches | 3 inches |
| diameter, first directional roll (2) | 2 inches | 2 inches |
| diameter, second directional roll (3) | 2 inches | 1 inch |
| diameter, third directional roll (4) | 3 inches | ⅝ inch |
| diameter, gravure roll (5) | 8 inches | ¾ inch |
| diameter, nip roll (6) | 8 inches | 1 inch |
| length, nip roll (6) | 11.5 inches | 3.5 inches |
| diameter, fourth directional roll (7) | 3 inches | none |
| diameter, fifth directional roll (8) | 3 inches | 1 inch |
| diameter, support rolls (9) | 2 inches | ½ inch |
| length, drying oven (24) | 15 feet | No oven |
| diameter, sixth directional roll (10) | 3 inches | 2 inches |
| diameter, seventh directional roll (11) | 8 inches | none |
| diameter, roll (12) | 6 inches | 2 inches |
| diameter, roll (13) | 6 inches | 1 inch |
| diameter, wind up roll (14) | 3 inches | 3 inches |
| substrate length, nip roll (6) to fourth directional roll (7) | 30 inches | none |
| Substrate length, fourth directional roll (7) to fifth directional roll (8) | 5 feet | none |
| Substrate length, nip roll (6) to fifth directional role (8) | 7.5 feet | 2.5 inches |
| Degree of vertical orientation, fourth directional roll (7) to fifth directional roll (8) | 80 degrees | N/A none |
| Degree of vertical orientation, nip roll (6) to fifth directional role (8) | N/A | 20 degrees |
| Substrate length within oven | 15 feet | no oven |
| Cell size, gravure roll | 120 Q | 110 Q |
| Length of gravure roll | 30 inches | 4 inches |

Substrate used in the Examples

The substrate was a heat-stabilized polyester film (polyethylene terephthalate (PET)) that was 0.005 inches thick (+/− 10%) and that had been metallized in a pattern consisting of metallized stripes (sputtered platinum or aluminum) 0.2675 inches wide and usable as electrodes alternating with gaps (nonmetallized sections) 0.020 inches wide. Other preferred plastic substrates include a polyimide such as Kapton®. The substrate must be able to withstand the highest temperatures used in the coating process and also provide a uniform coating surface. Metallization of the substrate is not required for creating a polymer film. However, a long sheet of substrate with a repeating metallized pattern can be cut into small pieces, each with the same metallized pattern, and the metallized pattern used as parts of an electrical circuit in the assembled sensor.

The width of the substrate was 3.75 inches on the small scale coater and 11.75 inches on the large scale coater. There are no inherent limits on the potential width of the film— they would depend on the availability of suitable substrate and the width of the coating machine and/or its coating head rolls.

The substrate was plasma-cleaned and inertly bagged under a nitrogen atmosphere in a hermetically sealed bag.

Due to the possibility of contaminating the metallized surface of the substrate, and by doing so, compromising the uniformity of the polymer coating, the interval between unwind and coating stations was kept as short as possible and the only roll in contact with the precoated surface was refinished to minimize the possibility of damage to the substrate.

The substrate length can be as small as desired by splicing the substrate to be coated into a longer sheet of substrate. For example, in one run on the small scale coater, a patterned metallized polyester substrate to be coated and measuring 6 inches in length was spliced into a nonmetallized polyester substrate. Similarly, the substrate length can be as long as can be adequately handled (several hundred feet, for example, in some large scale coater runs).

Polymer Solutions used in the Examples

The polymer used in the examples was poly(3-n-hexylthiophene) with an average degree of polymerization of about 1000. However, the nature of the invention is such that is applicable to a wide variety of polymers.

The polymer was synthesized by adding, in an inert atmosphere at 5° C., over 0.5 to 1 hour (times and other conditions denoted herein for polymer preparation are representative of conditions used but were not always exactly followed), the monomer dissolved in chloroform to a solution of ferric chloride in chloroform (final ratio of 0.5 kg anhydrous ferric chloride/5 to 6 L of chloroform). The molar ratio of catalyst to 3-n-hexylthiophene monomer was 4 to 1. Incubation was continued with stirring for about 2 hour. The majority of the ferric chloride was then extracted by multiple extractions with distilled water. The polymer was precipitated with methanol. Then the solid polymer was extracted in a Soxhlet apparatus with acetone for one week. The polymer was dissolved in toluene and washed with water. It was then filtered over a bed of Celite on top of alumina. It was then precipitated with methanol, collected by filtration, dried under vacuum, and stored as necessary in the dark.

Typically, the poly(3-hexylthiophene) was dissolved in a fresh solvent blend under nitrogen over the course of 24 hours to a concentration of 20 mg/ml. The solution was a 1.8% weight-to-volume solution of poly(3-n-hexylthiophene) in toluene/xylene at an 85/15 v/v ratio. There is no lower limit to the coatable concentration and the upper limit, for solubility reasons, is about 5%. The viscosity of the solution was very low, 2–4 cps (centipoise). Other solvents systems and solvent ratios may be used. No other constituents were in the coating solution but the use of thickeners, surfactants, modifiers, antioxidants, stabilizers, copolymers, dopants, or other chemical species to alter the physical or chemical properties of the solution is not precluded.

The solution was centrifuged, the supernatant collected and, using a coating apparatus, coated onto the substrate within 72 hours. Just prior to coating the substrate, the solution was diluted to the appropriate concentration, the platinized polyester film is unrolled and attached to substrate not to be coated that would precede it through the coating process (and when unwound from the unwind roll, attached to additional substrate not to be coated that would trail it through the process), the solution was introduced to the coating trough (22), the nip roll was engaged into contact with the substrate, and the film was coated with polymer solution.

Post-coating Handling

After passage through the oven (actually three contiguous ovens combined to create a single oven), the coated and dried film passed through the drive and rolls to the wind-up roll. Typically, the film was immediately unwound from the wind-up roll, sheeted, and interleaved with a cleaned polyethylene foam material, although it can be stored for at least four months in the rolled up state. Further converting (cutting) reduced the film to the appropriate size for incorporation into an electrochemical biosensor.

Example 3

Test for Uniformity of Coating of Substrate coater used: large scale line speed: 10 ft/min polymer: poly(3-n-hexylthiophene)

polymer concentration: about 17 mg/ml solvent: toluene:xylene::85:15 drying means: oven oven temperature: 200° F.

oven residence time: 90 seconds line speed for substrate: 10 ft/min substrate composition: 5 mil heat-stabilized polyester metal sputtered for metallization: platinum

RESULTS

As to visual uniformity, "Chatter lines" (roughly 1/40 inch thick) were present every 1/5 to 1/4 inches running parallel to the roller axes. The chatter lines are probably the result of machine vibration. Chatter lines, because they are essentially uniform across the width of the substrate, are probably not a significant contributor to nonuniformity of sensor response, as the electrodes can be cut from the substrate sheets in a manner that each well of the sensor has the same amount of chatter lines. "Substrate tension lines" were present every 2 to 4 inches roughly parallel to the roller axes and at one side of the substrate. The tension lines are probably due to periodic pulls and shifts on the substrate.

Fisheyes were observed over the entire material. Each fisheye was a series of concentric rings alternating in color intensity from lighter to darker (typically the central circle will be dark and have a diameter of about 1/16 inch, this will be surrounded by a lighter colored ring with an external diameter of about 1/8 inches, and that will be surrounded by a ring with an outer diameter of about 3/16 inches, the latter ring marking the outer edge of the fisheye.)

The amount of fisheyes were relatively infrequent (about one per 3 square inches).

No blocking was observed. The final product was interleaved with polyethylene foam. The film was not fragile (dragging a finger across it did not pull it off the substrate). The film was firm to the touch. The film was not tacky to the touch.

Example 4

Effect of Line Speed

This example was performed under essentially the same conditions as Example 3 except that the line speed was varied between 3 and 25 feet per minute and aluminum was used instead of platinum. Also, subsequent to the coating process, some of the coated substrate was baked for 15 minutes at 90° C. in an auxiliary oven. It was noted that slower speeds produced thinner films and higher speeds produced thicker films probably reflecting differences in the splitting of the solvent between the gravure roll and the substrate. At higher speeds it was also observed that machine noise and solution viscosities created more non-uniformity as evidenced by chatter and tension lines.

Fisheyes were relatively infrequent as in Example 3. Chatter and substrate tension lines were observed.

Example 5

Effect of Varying the Polymer Concentration

Example 3 was repeated except that the concentration of the coating solution was varied between 15 and 25 mg/ml and the oven temperature was about 78° C. It was observed that higher concentrations produce thicker films and lower concentrations produce thinner films. Higher and lower concentrations of poly(3-n-hexylthiophene) than those used in this example may be coated but they are generally not as preferred. As the films became thinner they evidenced more tendency towards nonuniformity.

Fisheyes were relatively frequent (about 12 per square inch). Chatter lines and substrate tension lines were observed.

Example 6

Effect of Changing the Solvent

Example 3 was repeated except that the binary solvent formulation used to dissolve and dilute the polymer was altered to include a third solvent, indan, and the oven temperature was about 78° C. That mixture was formulated in the solvent ratio of 85/10/5//toluene/xylene/indan. The ternary coatings appeared less fragile that the binary coatings and dried to a redder color and a flatter finish than the binary coatings.

The coating process was done on the same day and ambient conditions as Example 5. Fisheyes were relatively frequent (about 6 per square inch). Chatter lines and substrate tension lines were observed as in Example 5.

Example 7

Effect of Air Flow as Drying Means

In this example the small scale coater of FIG. 31 was used.

line speed: 3.1 ft/min polymer: poly(3-n-hexylthiophene)

polymer concentration: about 20 mg/ml solvent: toluene:xylene::85.15 substrate composition: 5 mil heat-stabilized polyester metal sputtered for metallization: aluminum An auxilary air dryer, sent air bar in FIG. 30. The direction of air flow was opposite to the direction of movement of the substrate. The air flow was directed against the polymer solution on the downwardly oriented side of the substrate, just as the substrate left the gravure roll (5). The air bars (30) were not used.

There were no fisheyes, chattering, tension lines. Tests were not made for blocking, fragility, or tackiness, or firmness, but there was no reason to believe that such test would show blocking, fragility, tacky film or unfirm film.

What is claimed is:

1. A gravure coating process, said process comprising, in the following sequence, the steps of:

(1) creating a solution comprising an electroconductive polymer dissolved in an organic solvent, (2) absorbing said solution onto a gravure surface of a cylinder, (3) transferring said solution directly from the gravure surface of the cylinder to a substrate surface, said surface being downwardly disposed, (4) evaporating the organic solvent from the solution transferred to the substrate surface so as to leave a film of the electroconductive polymer on the substrate surface wherein the substrate surface comprises a metallized pattern.

2. A process of claim 1 wherein after step (3) is completed and before step (4) is completed the substrate surface is oriented in a direction that has a vertical component.

3. A process of claim 1 wherein the evaporation in step (4) is accelerated by a applying a drying means to evaporate the solvent.

4. A process of claim 1 wherein the substrate surface is a flexible plastic substrate.

5. A gravure coating process, said process comprising, in the following sequence, the steps of:

(1) creating a solution comprising an electroconductive polymer dissolved in an organic solvent, (2) absorbing said solution onto a gravure surface of a cylinder, (3) transferring said solution directly from the gravure surface of the cylinder to a substrate surface, said surface being downwardly disposed, (4) evaporating the organic solvent from the solution transferred to the substrate surface so as to leave a film of the electroconductive polymer on the substrate surface wherein after step (3) is completed and before step (4) is completed, the substrate surface is oriented in a direction that has a vertical component and wherein the electroconductive polymer is selected from the group polyacetylene, polypyrrole, polythiophene, poly(3-alkylthiophene), polyphenylene sulfide, polyphenylene vinylene, polythienylene vinylene, polyphenylene, polyisothianaphthene, polyazulene, polyfuran, polyanaline, and derivatives of said polymers.

6. A gravure coating process, said process comprising, in the following sequence, the steps of:

(1) creating a solution comprising an electroconductive polymer dissolved in an organic solvent, (2) absorbing said solution onto a gravure surface of a cylinder, (3) transferring said solution directly from the gravure surface of the cylinder to a substrate surface, said surface being downwardly disposed, (4) evaporating the organic solvent from the solution transferred to the substrate surface so as to leave a film of the electroconductive polymer on the substrate surface wherein the evaporation in step (4) is accelerated by applying a drying means to evaporate the solvent and wherein the electroconductive polymer is selected from the group polyacetylene, polypyrrole, polythiophene, poly(3-alkylthiophene), polyphenylene sulfide, polyphenylene vinylene, polythienylene vinylene, polyphenylene, polyisothianaphthene, polyazulene, polyfuran, polyanaline, and derivatives of said polymers.

* * * * *